United States Patent
Choi et al.

(10) Patent No.: US 8,058,304 B2
(45) Date of Patent: Nov. 15, 2011

(54) MERGED ION CHANNEL MODULATING COMPOUNDS AND USES THEREOF

(75) Inventors: Lewis S. L. Choi, Burnaby (CA); Doug Ta Hung Chou, Vancouver (CA); Grace Jung, New Westminster (CA); Bertrand M. C. Plouvier, Vancouver (CA)

(73) Assignee: Cardiome Pharma Corp., Vancouver, BC (CA)

( * ) Notice: Subject to any disclaimer, the term of this patent is extended or adjusted under 35 U.S.C. 154(b) by 772 days.

(21) Appl. No.: 11/547,422

(22) PCT Filed: Apr. 1, 2005

(86) PCT No.: PCT/US2005/011103
§ 371 (c)(1),
(2), (4) Date: Sep. 30, 2008

(87) PCT Pub. No.: WO2005/097087
PCT Pub. Date: Oct. 20, 2005

(65) Prior Publication Data
US 2009/0088464 A1   Apr. 2, 2009

Related U.S. Application Data

(60) Provisional application No. 60/559,375, filed on Apr. 1, 2004, provisional application No. 60/587,005, filed on Jul. 8, 2004.

(51) Int. Cl.
*A61K 31/40* (2006.01)
*C07D 207/00* (2006.01)

(52) U.S. Cl. .................................... 514/424; 548/541
(58) Field of Classification Search .................. 548/541; 514/424
See application file for complete search history.

(56) References Cited

U.S. PATENT DOCUMENTS

| | | | |
|---|---|---|---|
| 2,954,380 A | 9/1960 | Shapiro et al. | 260/268 |
| 3,218,328 A | 11/1965 | Shapiro et al. | 260/294 |
| 4,145,435 A | 3/1979 | Szmuszkovicz | 424/274 |
| 4,179,501 A | 12/1979 | Szmuszkovicz | 424/226 |
| 4,188,403 A | 2/1980 | Orth et al. | 424/330 |
| 4,598,087 A | 7/1986 | Horwell | 514/424 |
| 4,656,182 A | 4/1987 | Horwell | 514/324 |
| 4,663,343 A | 5/1987 | Horwell et al. | 514/429 |
| 4,855,316 A | 8/1989 | Horwell et al. | 514/422 |
| 4,880,800 A | 11/1989 | Wallis et al. | 514/211 |
| 4,906,655 A | 3/1990 | Horwell et al. | 514/422 |
| 5,019,588 A | 5/1991 | Horwell et al. | 514/409 |
| 5,051,428 A | 9/1991 | Horwell et al. | 514/320 |
| 5,059,620 A | 10/1991 | Stout et al. | 514/422 |
| 5,492,825 A | 2/1996 | Jan et al. | 435/240.2 |
| 5,506,257 A | 4/1996 | MacLeod et al. | 514/422 |
| 5,637,583 A | 6/1997 | MacLeod et al. | 514/212 |
| 5,670,335 A | 9/1997 | Jan et al. | 435/29 |
| 5,728,535 A | 3/1998 | Lester et al. | 435/7.2 |
| 5,734,021 A | 3/1998 | Lester et al. | 530/350 |
| 5,750,537 A | 5/1998 | Nomura et al. | 514/304 |
| 5,817,698 A | 10/1998 | Brown et al. | 514/646 |
| 5,885,984 A | 3/1999 | MacLeod et al. | 514/211 |
| 6,174,879 B1 | 1/2001 | MacLeod et al. | 514/212.01 |
| 6,180,632 B1 | 1/2001 | Myers et al. | 514/252.1 |
| 6,210,809 B1 | 4/2001 | Okutomi et al. | 428/546 |
| 6,214,810 B1 | 4/2001 | Fermini et al. | 514/75 |
| 6,451,819 B2 | 9/2002 | Alanine et al. | 514/326 |
| 6,521,619 B2 | 2/2003 | Link et al. | 514/237.2 |
| 6,649,603 B2 | 11/2003 | Sum | 514/210.01 |
| 6,979,685 B1 | 12/2005 | Beatch et al. | 514/231.2 |
| 7,053,087 B1 | 5/2006 | Beatch et al. | 514/237.8 |
| 7,057,053 B2 | 6/2006 | Beatch et al. | 548/541 |
| 7,101,877 B2 * | 9/2006 | Bain et al. | 514/231.2 |
| 7,259,184 B2 | 8/2007 | Beatch et al. | 514/424 |
| 7,345,086 B2 | 3/2008 | Beatch et al. | 514/424 |
| 7,345,087 B2 * | 3/2008 | Beatch et al. | 514/424 |
| 7,507,545 B2 | 3/2009 | Fedida et al. | 435/7.2 |
| 7,524,879 B2 | 4/2009 | Beatch et al. | 514/424 |
| 7,534,790 B2 * | 5/2009 | Bain et al. | 514/231.2 |
| 7,875,611 B2 | 1/2011 | Bain et al. | 514/239.5 |
| 2005/0002693 A1 | 1/2005 | Pak et al. | 399/165 |
| 2005/0038256 A1 | 2/2005 | Barrett et al. | 546/236 |
| 2005/0070552 A1 | 3/2005 | Fedida et al. | 514/255.06 |
| 2006/0252753 A1 | 11/2006 | Beatch et al. | 514/237.8 |

(Continued)

FOREIGN PATENT DOCUMENTS

CA   1234808   4/1988

(Continued)

OTHER PUBLICATIONS

Billman et al., 2003, CAS: 139:270094.*
Or Bain et al., 1999, CAS:131:257571.*
Adcock et al., "RSD931, a novel anti-tussive agent acting on airway sensory nerves", *Br J Pharm* 138(3):407-416, 2003.
Altria et al., "Capillary Electrophoresis as a Routine Analytical Tool in Pharmaceutical Analysis", *LCGC* 19(9): 972-985, Sep. 2001.
Amin et al., "RPR 101821, a New Potent Cholesterol-lowering Agent: Inhibition of Squalene Synthase and 7-Dehydrocholesterol Reductase", *Naunyn-Schmiedeberg's Arch Pharmacol* 353:233-240, 1996.

(Continued)

*Primary Examiner* — Rei-tsang Shiao
(74) *Attorney, Agent, or Firm* — Seed IP Law Group PLLC

(57) ABSTRACT

Merged compounds of ion channel modulating compounds, including, for example, merged compounds of the ion channel modulating compound of the following formula: (I) are described herein, as well as methods of making and using such merged compounds and pharmaceutical compositions containing such merged compounds.

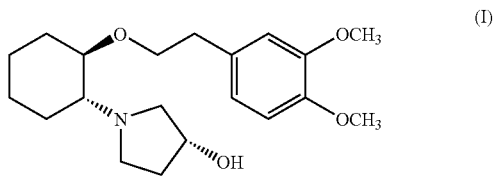

(I)

16 Claims, No Drawings

U.S. PATENT DOCUMENTS

| | | | |
|---|---|---|---|
| 2007/0099983 A1 | 5/2007 | Barrett et al. | 514/408 |
| 2007/0190156 A1 | 8/2007 | Beatch et al. | 424/489 |
| 2007/0197632 A1 | 8/2007 | Beatch et al. | 514/327 |
| 2007/0254945 A1 | 11/2007 | Jung et al. | 514/424 |
| 2009/0105256 A1 | 4/2009 | Choi et al. | 514/237.2 |
| 2010/0056603 A1 | 3/2010 | Beatch et al. | 514/424 |

FOREIGN PATENT DOCUMENTS

| | | |
|---|---|---|
| CA | 1235122 | 4/1988 |
| CA | 1243020 | 10/1988 |
| CA | 2004575 | 6/1990 |
| CA | 2058502 | 6/1993 |
| CA | 2172513 | 3/1995 |
| CA | 2244209 A1 | 7/1997 |
| CA | 2008391 | 12/1997 |
| CA | 2289055 A1 | 1/1999 |
| CA | 2268590 A1 | 10/2000 |
| CA | 2132841 | 3/2001 |
| DE | 2 259 260 | 6/1974 |
| DE | 2 658 401 | 7/1978 |
| DE | 3 517 901 A1 | 12/1985 |
| EP | 222533 A1 | 5/1987 |
| EP | 147085 B1 | 3/1990 |
| EP | 372466 A2 | 6/1990 |
| EP | 380063 B1 | 8/1990 |
| EP | 0 546 583 A1 | 6/1993 |
| EP | 552386 A1 | 7/1993 |
| EP | 720605 B1 | 7/1996 |
| HU | 215963 B | 2/1995 |
| JP | 02-270864 | 11/1990 |
| WO | WO 93/19056 | 9/1993 |
| WO | WO 94/07843 A1 | 4/1994 |
| WO | WO 94/14435 A1 | 7/1994 |
| WO | WO 95/08544 A1 | 3/1995 |
| WO | WO 95/28155 A1 | 10/1995 |
| WO | WO 96/18615 A1 | 6/1996 |
| WO | WO 96/23894 A1 | 8/1996 |
| WO | WO 97/32857 A1 | 9/1997 |
| WO | WO 97/49680 A1 | 12/1997 |
| WO | WO 98/40055 A2 | 9/1998 |
| WO | WO 99/02159 A1 | 1/1999 |
| WO | WO 99/03468 A1 | 1/1999 |
| WO | WO 99/11252 A2 | 3/1999 |
| WO | WO 99/16431 A1 | 4/1999 |
| WO | WO 99/50205 A2 | 10/1999 |
| WO | WO 99/50225 A1 | 10/1999 |
| WO | WO 00/23023 A1 | 4/2000 |
| WO | WO 00/47547 A2 | 8/2000 |
| WO | WO 00/51981 A1 | 9/2000 |
| WO | WO 01/51474 A2 | 7/2001 |
| WO | WO 01/96335 A1 | 12/2001 |
| WO | WO 02/18334 A2 | 3/2002 |
| WO | WO 03/105756 A2 | 12/2003 |
| WO | WO 2004/008103 A2 | 1/2004 |
| WO | WO 2004/098525 A2 | 11/2004 |
| WO | WO 2004/099137 A1 | 11/2004 |
| WO | WO 2005/018635 A2 | 3/2005 |
| WO | WO 2005/094897 A2 | 10/2005 |
| WO | WO 2005/113011 A2 | 12/2005 |

OTHER PUBLICATIONS

Alzheimer's Disease Information Page [online], [retrieved on Oct. 3, 2006]. Retrieved from the Internet, URL: <http://www.ninds.nih.gov/disorders/alzheimersdisease/alzheimersdisease.htm>.

Asensio et al., "Epoxidation of Primary and Secondary Alkenylammonium Salts with Dimethyldioxirane, Methyl(trifluoromethyl)dioxirane, and m-Chloroperbenzoic Acid. A General Synthetic Route to Epoxyalkylamines", *J. Org. Chem.* 60(12): 3692-3699, 1995.

Bain et al., "Better Antiarrhythmics? Development of Antiarrhythmic Drugs Selective for Ischaemia-Dependent Arrhythmias", *Drug Development Research* 42:198-210, 1997.

Bakalarz-Jeziorna et al., "Synthesis of multifunctionalized phosphonic acid esters via opening of oxiranes and azetidinium salts with phosphoryl-substituted carbanions", *J. Chem. Soc., Perkin Trans. 1*: 1086-1090, 2001.

Barrett and Walker, "Glibenclamide Possesses Transient, Ischaemia Selective Class III Antiarrhythmic Actions But Does Not Prevent Ischaemic Arrhythmias", *BPS Proceedings* 116P, 1996.

Barrett et al., "A Model of Myocardial Ischemia for the Simultaneous Assessment of Electrophysiological Changes and Arrhythmias in Intact Rabbits", *J Pharmacol Toxicol Methods* 37(1):27-36, 1997.

Barrett et al., "Ischaemia selectivity confers efficacy for suppression of ischaemia-induced arrhythmias in rats", *Eur J Pharm* 398:365-374, 2000.

Barrett et al., "Atypical Dose Response Curves for Antiarrhythmic Drugs", *BPS Proceedings* 115P, 1996.

Barrett, "Ischemia Selective Electrophysiological and Antiarrhythmic Actions of RSD1019 in Ischemic Cardiac Tissue", *J Mol Cell Cardiol* 29:197, 1997.

Barrett et al., "RSD1019 suppresses ischaemia-induced monophasic action potential shortening and arrhythmias in anaesthetized rabbits", *Br J Pharm* 131(3):405-414, 2000.

Beatch et al., "RSD1235 Selectively Prolongs Atrial Refractoriness and Terminates AF in Dogs with Electrically Remodelled Atria", *Pharmacologist* 44(2) (Supp I), A15: XIVth World Congress of Pharmacology: Meeting Abstracts, 2002. Abstract No. 22.11.

Beatch et al., "Effect of a Novel Anti-tussive Compound CP1 Against Citric Acid Induced Cough in Guinea-Pigs", *Proc West Pharmacol Soc* 44:252, 2001.

Beatch et al., "RSD1235 Rapidly and Effectively Terminates Atrial Fibrillation", Abstract submission ESC Congress Aug. 30-Sep. 3, 2003, in Vienna, Austria.

Beatch et al., "RSD1235, A Novel Atrial-Selective Antiarrhythmic Drug, Shows Rapid and Extensive Oral Absorption in Man", 12th International Congress on Cardiovascular Pharmacotherapy, May 7-10, 2003, Barcelona, Spain.

Beatch et al., "Ventricular Fibrillation, an Uncontrolled Arrhythmia Seeking New Targets", *Drug Develop Res* 55:45-52, 2002.

Beatch, "Antihistamine-induced Ventricular Arrhythmias", *BPS Proceedings* 120P, 1996.

Beatch et al., "Characterization of a Non-Human Primate Model of Drug-Induced Torsades De Pointes", *Proc West Pharmacol Soc* 40:13-16, 1997.

Beatch et al., "RSD1235 Selectively Prolongs Atrial Refractoriness and Terminates AF in Dogs with Electrically Remodelled Atria", *PACE* 24(Part II):698. Abstract 702, May 10, 2002.

Bian et al., "Effects of Kappa-opioid receptor stimulation in the heart and the involvement of protein kinase C", *Brit J Pharm* 124:600-606, 1998.

Billman, "RSD-1235", *Curr Opin Investigational Drugs* 4(3):352-354, 2003.

Boiadjiev and Lightner, "pH-Sensitive Exciton Chirality Chromophore. Solvatochromic Effects on Circular Dichroism Spectra", *Tetrahedron: Asymmetry* 7(10):2825-2832, 1996.

Bowen et al., "Characterization of the Enantiomers of cis-N-[2-(3,4-Dichlorophenyl)Ethyl]-N-Methy1-2-(1-Pyrrolidinyl)Cyclohexylamine (BD737 and BD738): Novel Compounds with High Affinity, Selectivity and Biological Efficacy at Sigma Receptors", *J Pharmacol Exp Ther* 262(1):32-40, 1992.

Cardiome Pharma Corp. (Jan. 31, 2001). "Nortran Drug Effective in Atrial Arrhythmia Model" (http://cardiome.com/wordpress/?p=104). Press Release.

Cardiome Pharma Corp. (Jun. 21, 2001). "Nortran Antiarrhythmia Drug Demonstrates Oral Bioavailability" (http://cardiome.com/wordpress/?p=99). Press Release.

Cardiome Pharma Corp. (Jul. 30, 2001). "Cardiome Pharma Completes Phase I Safety Study" (http://cardiome.com/wordpress/?p=97). Press Release.

Cardiome Pharma Corp. (Jan. 17, 2002). "Cardiome Reports Dosing of First Patient in Pivotal Phase II Study" (http://cardiome.com/wordpress/?p=90). Press Release.

Cardiome Pharma Corp. (Sep. 3, 2002). "Cardiome Drug Effective for Heart Patients" (http://cardiome.com/wordpress/?p=75). Press Release.

Cardiome Pharma Corp. (Dec. 5, 2002). "Cardiome Reports Oral Absorption of RSD1235 in Humans" (http://cardiome.com/wordpress/?p=72). Press Release.

Cardiome Pharma Corp. (Dec. 20, 2004). "Cardiome's Pivotal AF Study Achieves Primary Endpoint" (http://cardiome.com/wordpress/?p=14). Press Release.
Cardiome Pharma Corp. (Feb. 4, 2005). "Cardiome Reports Additional ACT 1 Clinical Results" (http://cardiome.com/wordpress/?p=2). Press Release.
Cardiome Pharma Corp. (Apr. 25, 2005). "Cardiome Successfully Completes Second Phase 1 Trial" (http://cardiome.com/wordpress/?p=230). Press Release.
Cardiome Pharma Corp. (Aug. 31, 2005). "Cardiome Successfully Completes RSD1235 Oral Phase 1 Trial" (http://cardiome.com/wordpress/?p=255). Press Release.
Cardiome Pharma Corp. (Sep. 29, 2005). "Cardiome and Astellas Announce Positive Results from Second Phase 3 Trial" (http://cardiome.com/wordpress/?p=262). Press Release.
Cardiome Pharma Corp. (May 5, 2006). "Cardiome Reports Additional Phase 1 Trial Data for Oral RSD1235" (http://cardiome.com/wordpress/?p=291). Press Release.
Cardiome Pharma Corp. (Jul. 24, 2006). "Cardiome Announces Interim Phase 2A Results for Oral RSD1235" (http://cardiome.com/wordpress/?p=312). Press Release.
Cardiome Pharma Corp. (Sep. 13, 2006). "Cardiome Announces Positive Phase 2A Results for Oral RSD1235" (http://cardiome.com/wordpress/?p=321). Press Release.
Cardiome Pharma Corp. Healthcare (Underweight) Company Report Dec. 12, 2002. 26 pages.
Carmeliet and Mubagwa, "Antiarrhythmic drugs and cardiac ion channels: mechanisms of action", *Progress in Biophysics & Molecular Biology* 70: 1-72, 1998.
Clohs and Wong, "Validation of a capillary electrophoresis assay for assessing the metabolic stability of verapamil in human liver microsomes", *J Cap Elec & Microchip Tech* 007(5/6):113-117, 2002.
Clohs, "Capillary Electrophoresis and Its Applications in the Pharmaceutical Industry—Short Course: One Platform Fits Many Applications", CSC 2002, 52 pages.
Clohs, "Capillary Electrophoresis as an Analytical Tool in the Drug Discovery Process", Presentation CE Symposium, Aug. 2000, 40 pages.
Clohs, "The Versatility of CE for Drug Pharmacokinetics and Metabolism Studies", CE in the Biotechnology & Pharmaceutical Industries (Symposium), Boston, Aug. 2001, 46 pages.
Clohs, "Pharmacokinetics profiling of new drug candidates: a key process in drug discovery", *Beckman Coulter P/ACE Setter* 4(1):6, Jun. 2000.
Clohs and Winstanley, "CE Analysis of Propranolol in Human Serum Using Dynamic Capillary Coating", *CE Currents: LCGC Europe*, Reader Service 14, pp: 289-293, May 2002.
Clohs, "Bio-Analytical Applications of Capillary Electrophoresis in a Drug Discovery Setting", CSC Seminar, Jun. 5, 2002, 29 pages.
Clohs, "CE and Drug Metabolism Studies: A Powerful Combination in Drug Discovery", CE in the Biotechnology and Pharmaceutical Industries (Symposium), Washington, DC, Aug. 2002, 31 pages.
Crotti et al., "Regiochemical control of the ring-opening of epoxides by means of chelating processes Part 13 . . . ", Chemical Abstracts 129(17):662-663, Abstract No. 216472k, 1998.
Crotti et al., "Synthesis and Ring-Opening Reactions of the Diastereoisomeric cis- and trans-Epoxides Derived from 3-(Benzyloxy)cyclopentene and 2-(Benzyloxy)-2,5-dihydrofuran", *Eur J Org Chem* 8:1675-1686, 1998.
Curtis and Walker, "Quantification of arrhythmias using scoring systems: an examination of seven scores in an in vivo model of regional myocardial ischaemia", *Cardiovascular Research* 22: 656-665, 1988.
De Costa et al., "Synthesis and Evaluation of N-Substituted cis-N-Methyl-2-(1-pyrrolidinyl)cyclohexylamines as High Affinity σ Receptor Ligands. Identification of a New Class of Highly Potent and Selective σ Receptor Probes", *J Med Chem* 33:3100-3110, 1990.
Doci et al., "Local Anesthetic Effects of Intradermal RSD921 in Healthy Subjects", Proceedings of the 100th Annual Meeting of the American Society for Clinical Pharmacology and Therapeutics, San Antonio, Texas, Mar. 18-20, 1999, Abstract PIII-2 in *Clin Pharm & Therap* 65(2):177, Feb. 1999.

Duan et al., "Potassium Channel Blocking Properties of Propafenone in Rabbit Atrial Myocytes", *J Pharm Exp Ther* 264(3): 1113-1123, 1993.
Ezrin et al., "Safety and Pharmacokinetics of RSD1235, a Novel Atrial Fibrillation Converting Drug, in Healthy Volunteers", Abstracts: 11th Int. Congress Cardiovasc. Pharmacother. 16 Abstract P297, 2002.
Ezrin et al., "A Dose-Ranging Study of RSD1235, A Novel Antiarrhythmic Agent, in Healthy Volunteers", Pharmacologist, 44(2) (Supplement I), A15: XIVth World Congress of Pharmacology: Meeting Abstracts, 2002. Abstract No. 22.10.
Fedida et al., "Kv1.5 is an Important Component of Repolarizing $K^+$ Current in Canine Atrial Myocytes", Circulation Research Peer Review Plus Manuscript PDF, 38 pages, 2002.
Franciosi et al., "Phase II Clinical Trial of RSD921 as a Local Anaesthetic in Patients Undergoing Venous Cannulation for Elective Treatment", in Proceedings of the 28th Annual ACCP Meeting Abstract 32, p. 977, Feb. 2000.
Franciosi and McLarnon, "pH-dependent blocking actions of three novel antiarrhythmic compounds on $K^+$ and $Na^+$ currents in rat ventricular myocytes", *Eur J Pharm* 425:95-107, 2001.
Franqueza et al., "Effects of propafenone and 5-hydroxy-propafenone on hKv1.5 channels", *Br J Pharm* 125:969-978, 1998.
Friess et al., "Central Activity Evoked in the Cat by Cis-Trans Isomers of 1,2-Aminocyclohexanol Derivativites", *Taxicol Appl Pharmacol* 3:638-653, 1961.
Grant, "Mechanisms of Atrial Fibrillation and Action of Drugs Used in its Management", *Am J Cardiol* 82:43N-49N, Oct. 16, 1998.
Gund, "Three-Dimensional Pharmacophoric Pattern Searching," in Hahn et al. (eds.), Progress in Molecular and Subcellular Biology, Springer-Verlag, Berlin, Germany, 1977, pp. 117-143.
Halfpenny et al., "Highly Selective k-Opioid Analgesics. 3. Synthesis and Structure-Activity Relationships of Novel N-[2-(1-Pyrrolidinyl)-4- or -5-substituted-cyclohexyl]arylacetamide Derivatives", *J Med Chem* 33:286-291, 1990.
Halfpenny et al., "Highly Selective k-Opioid Analgesics. 2. Synthesis and Structure-Activity Relationships of Novel N-[(2-Aminocyclohexyl)aryl]acetamide Derivatives", *J Med Chem* 32:1620-1626, 1989.
Hayes et al., "RSD 992 Enhances Erection and Copulation in Rats and Erection in Primates", *Int J Impotence Res* p. 189 (Abstract P24), 1996.
Hayes et al., "Actions of Arylpiperazines on Corpus Cavernosum Smooth Muscle in Vitro", *Asia Pac J Pharmacol* 12:97-103, 1997.
Hayes et al., "Direct Actions of Arylpiperazines on Rabbit and Human Corpus Caversonal Smooth Muscle in Vitro", *Asia Pac J Pharmacol*, Abstract S15, 1997.
Hesketh et al., "Safety of RSD1235 in a rabbit Purkinje fiber model", in Proceedings of the XIVth World Congress of Phar. Meeting, Abstract No. 22.12, 2002.
Hou et al., "Synthesis of novel and enantiomerically pure epoxypropylamine: a divergent route to the chiral β-adrenergic blocking agents", *Tetrahedron: Asymmetry* 10: 2319-2326, 1999.
Howard and Walker, "Electrical Stimulation Studies with Quinacainol, a Putative IC Agent, in the Anaesthetised Rat", *Proc. West. Pharmacol. Soc.* 33: 123-127, 1990.
Iwasaki et al., "Chemo- and Stereoselective Monobenzoylation of 1,2-Diols Catalyzed by Organotin Compounds", *J. Org. Chem.* 65(4): 996-1002, 2000.
Keefe et al., "New Antiarrhythmic Drugs: Their Place in Therapy", *Drugs* 22:363-400, 1981.
Kertesz et al., "The Electrophysiological and Antiarrhythmic Actions of RSD Analogs of U50,488H in Rats", in Proceedings of the West Pharmacol Soc. 9 pages, 1994.
Lang et al., "Clinical Evaluation of RSD921 As a Local Anaesthetic in Patients Undergoing Venous Cannulation for Elective Treatment", *Clin Pharm & Therapeutics*, p. 142, Feb. 2000. Abstract PIII-1.
Lewis et al., "Enzyme inhibition during the conversion of squalene to cholesterol", *Steroids* 60:475-483, Jul. 1995.
Li et al., "Adrenergic Modulation of Ultrarapid Delayed Rectifier $K^+$ Current in Human Atrial Myocytes", *Circ Res* 78(5):903-915, May 1996.

Malayev et al., "Mechanism of Clofilium Block of the Human Kv1.5 Delayed Rectifier Potassium Channel", *Mol Pharm* 47:198-205, 1995.

Martens et al., "Einfache Synthese neuer anellierter Pyrrole", *J Synth Org Chem* 12:965-967, Dec. 1989.

Mátyus et al., "Antiarrhythmic Agents: Current Status and Perspectives", *Medicinal Research Reviews* 17(5):427-451, 1997.

McLarnon et al., "Mixed Block of $K^+$ and $Na^+$ Currents by KC8851, A Structural Analogue of Tedisamil in Vitro and in Vivo Studies", *BPS Proceedings* 114P, 1996.

Moorman et al., "$pK_a$ Does Not Predict pH Potentiation of Sodium Channel Blockade by Lidocaine and W6211 in Guinea Pig Ventricular Myocardium", *The Journal of Pharmacology and Experimental Therapeutics* 238(1):159-166, 1986.

Morisawa et al., "Preparation of fluorocarbocyclic nucleosides as antitumor agents", Chemical Abstracts 115(5):904-905, abstract No. 50215n, 1991.

Nakashima et al., "Angiotensin II Type I Receptor Antagonist Prevents the Promotion of Atrial Fibrillation", *PACE* 24(Part II):698, May 10, 2002. Abstract 701.

Nattel et al., "Effects of the novel antiarrhythmic agent azimilide on experimental atrial fibrillation and atrial electrophysiologic properties", *Cardiovascular Research* 37:627-635, 1998.

Nattel et al., "RSD1235: a novel antiarrhythmic agent with a unique electrophysiological profile that terminates AF in dogs", *Eur Heart J* 22(Suppl):448 (Abstract P2362), 2001.

Nattel, "Experimental evidence for proarrhythmic mechanisms of antiarrhythmic drugs", *Cardiovascular Research* 37:567-577, 1998.

Nattel et al., "The Role of Channel Opening in Transient Outward Current Block by Quinidine, Flecainide, and 4-Aminopyridine in Human Atrial Myocytes", K Channels II: Regulation and Block, Abstract No. Tu-Pos403, 1994.

Nishi et al., "Studies on 2-Oxoquinoline Derivatives as Blood Platelet Aggregation Inhibitors. IV. Synthesis and Biological Activity of the Metabolites of 6-[4-(1-Cyclohexyl-1H-5-tetrazolyl)butoxy]-2-oxo-1,2,3,4-tetrahydroquinoline (OPC-13013)", *Chem Pharm Bull* 33(3):1140-1147, 1985.

Orth et al., "Cyclopentane-1-amines", Chemical Abstracts 89(15):555, Abstract No. 129113f, 1978.

Orth et al., "The Novel AF Conversion Agent RSD1235 Preferentially Blocks a Late Component of the Human Heart (hHl) $Na^+$ Current Active During Repolarization", EP Abstracts Oct. 3, 2003.

Page, "Beta-Blockers for Atrial Fibrillation: Must We Consider Asymptomatic Arrhythmias?", *Journal of the American College of Cardiology* 36(1): 147-150, Jul. 2000.

Panfilov et al., "Reactions of Sodium Borohydride in Acetic Acid: Reductive Amination of Carbonyl Compounds", *Pharmaceutical Chemistry Journal* 34(7): 371-373, 2000.

Pugsley and Goldin, "Molecular analysis of the $Na^+$ channel blocking actions of the novel class I antiarrhythmic", *Br J Pharm* 127:9-18, 1999.

Pugsley et al., "A Characterization of the Antiarrhythmic and Electrophysiological Properties of RSD992, A Novel Arylpiperazine Drug", XIVth World Congress of Pharmacology: Meeting Abstract 22.8, in Pharmacologist 44(2, Supp 1):A15, 2002.

Pugsley et al., "Electropharmacology of Two New Class 1 agents", Heart and Stroke Annual Conference, p. 12, 1995.

Pugsley et al., "Sodium Channel-Blocking Properties of Spiradoline, a Kappa Receptor Agonist, are Responsible for Its Antiarrhythmic Action in the Rat", *J Cardiovas Pharmacol* 32:863-874, 1998.

Pugsley et al., "Are the arrhythmias due to myocardial ischaemia and infarction dependent upon the sympathetic system?", *Cardiol Res* 43:830-831, 1999.

Ribeiro et al., "Determination of RSD921 in human plasma by high-performance liquid chromatography-tandem mass spectrometry using tri-deuterated RSD921 as internal standard: application to a phase I clinical trial", *J Mass Spectrom* 36:1133-1139, 2001.

Rich et al., "Quinidine Block of the Human Cardiac hKv1.5 Channel in Inside-Out Patches, K Channels II: Regulation and Block", Abstract No. Tu-Pos404, p. A209, 1999.

Roden and George, "The Cardiac Ion Channels: Relevance to Management of Arrhythmias", *Annu Rev Med* 47:135-148, 1996.

Roy et al., "RSD1235 Rapidly and Effectively Terminates Atrial Fibrillation", *Eur-Heart J*, p. 3699, 2003.

Rynbrandt et al., "Cis-1-[2-(p-Anisidinomethyl) cyclohexyl] piperidine and Related Compounds. Oral Hypoglycemic Agents", *J Med Chem* 14 (10): 985-987, 1971.

Sanguinetti, "Modulation of Potassium Channels by Antiarrhythmic and Antihypertensive Drugs", *Hypertension* 19(3):228-236, Mar. 1992.

Singh, "Antiarrhythmic Drugs: A Reorientation in Light of Recent Developments in the Control of Disorders of Rhythm", *Am J Cardiol* 81(6A):3D-13D, Mar. 19, 1998.

Singh, "Atrial Fibrillation: Epidemiologic Considerations and Rationale for Conversion and Maintenance of Sinus Rhythm", *J Cardiovasc Pharmacol Therapeut* 8(Supp 1):S13-S26, 2003.

Snyders et al., "A Rapidly Activating and Slowly Inactivating Potassium Channel Cloned from Human Heart", *J. Gen. Physiol.* 101:513-543, Apr. 1993.

Snyders and Yeola, "Determinants of Antiarrhythmic Drug Action—Electrostatic and Hydrophobic Components of Block of the Human Cardiac hKv1.5 Channel", *Circ Res* 77(3):575-583, Sep. 1995.

Srilatha et al., "Alterations in Rabbit Corpus Cavernosal Pharmacology by High Cholesterol Diet", *Asia Pac J Pharmacol*, Abstract S15, 1997.

Steinbeck, "Proarrhythmische Wirkungen von Antiarrhythmika—Theoretische und Klinische Aspekte", *Z Kardiol* 81(Supp 4):139-143, 1992.

Stevenson, "Atrial Fibrillation and Heart Failure—Five More Years", *N Engl J Med* 351(23):2437-2440, Dec. 2, 2004.

Stoschitzky et al., "Racemic beta-blockers—fixed combinations of different drugs," *J. Clin. Bas. Cardiology* 1: 14-18, 1998.

Tong et al., "Determination of an arylether antiarrhythmic and its N-dealkyl metabolite in rat plasma and hepatic microsomal incubates using liquid chromatography-tandem mass spectrometry", *J Chromatog B* 759:259-266, 2001.

Valenzuela et al., "Comparative effects of nonsedating histamine $H_1$ receptor antagonists, ebastine and terfenadine, on human Kv1.5 channels", *Eur J Pharm* 326:257-263, 1997.

Valenzuela et al., "Effects of Ropivacaine on a Potassium Channel (hKv1.5) Cloned from Human Ventricle", *Anesthesiology* 86:718-728, 1997.

Walker, "Antiarrhythmic Drug Development—Illusion and Disillusion?", *Drug Develop Res* 55:1-2, 2002.

Walker et al., "Determination of an arylacetamide antiarrhythmic in rat blood and tissues using reversed-phase high-performance liquid chromatography", *J Chromatog B* 675:257-263, 1996.

Walker et al., "Increased Electrophysiological Activity in Raised $K^+$ and low pH Improves Antiarrhythmic Efficacy for a Group of Morpholinocyclohexyl Derivatives", *BPS Proceedings* 118P, 1996.

Walker and Guppy, "Targeting Ischemic Ventricular Arrhythmias", Cardiac Drug Development Guide, Humana Press Inc., Totowa, NJ, pp. 175-201, 2003.

Wang et al., "Effects of Flecainide, Quinidine, and 4-Aminopyridine on Transient Outward and Ultrarapid Delayed Rectifier Currents in Human Atrial Myocytes", *J Pharm Exp Ther* 272(1):184-196, 1995.

Wang et al., "Sustained Depolarization-Induced Outward Current in Human Atrial Myocytes", *Circ Res* 73(6):1061-1076, Dec. 1993.

Wat et al., "Effects of Arylbenzacetamides on Neuromuscular Preparation", *Proc West Pharmacol Soc* 1994.

Wolf et al., "Impact of Atrial Fibrillation on Mortality, Stroke, and Medical Costs", *Arch Intern Med* 158: 229-234, Feb. 9, 1998.

Wong and Clohs, "Protein Binding Study of AA5, a New Antiarrhythmic Drug", Nortran Pharmaceuticals Inc., Vancouver, BC, Poster Conference, Aug. 2000.

Wong and Clohs, "Capillary Electrophoresis Assay to Assess in Vitro Metabolic Stability of Novel Compounds in Human Liver Microsomes", Cardiome Pharma Corp., Vancouver, BC, AAPS Poster, Oct. 2001.

Yeola et al., "Molecular Analysis of a Binding Site for Quinidine in a Human Cardiac Delayed Rectifier $K^+$ Channel—Role of S6 in Antiarrhythmic Drug Binding", *Circ Res* 78(6): 1105-1114, Jun. 1996.

Yong et al., "Low pKa Predicts Antiarrhythmic Efficacy in a Series of Aminocyclohexyl Esters", *J Mol Cell Cardiol*, Abstract 057, 1997.

Yong et al., "RSD1000: A Novel Antiarrhythmic Agent with Increased Potency Under Acidic and High-Potassium Conditions", *J Pharm Exp Ther* 289(1):236-244, 1999.

Yong et al., "RSD1000: A Novel Antiarrhythmic Agent with an Improved Therapeutic Index", *BPS Proceedings* 119P, 1996.

Yong et al., "SAR Evidence that Antiarrhythmic Activity is Unrelated to Opioid Kappa Agonist Activity", *BPS Proceedings* 117P, 1996.

Zhang et al., "Inhibition of [$^3$H]-U69593 binding and the cardiac effects of U50, 488H by calcium channel blockers in the rat heart", *Brit J Pharmacol* 120:827-832, 1997.

Zolotoy et al., "Physicochemical Determinants for Drug Induced Blockade of HERG Potassium Channels: Effect of Charge and Charge Shielding", *Curr Med Chem* 1(3): 1-17, 2003.

Plouvier et al., "Synthesis and Structure Activity Relationships of a Series of 2-Aminocyclohexyl Esters as Potential Ischaemia Selective Ventricular Antiarrhythmics," BMPS 994, 85th CSC Conference & Exhibition, Vancouver, British Columbia, Canada, Jun. 1-5, 2002, 1 page.

* cited by examiner

MERGED ION CHANNEL MODULATING COMPOUNDS AND USES THEREOF

CROSS-REFERENCE TO RELATED APPLICATIONS

This application is a U.S. National Phase Application of International Application No. PCT/US2005/011103, filed Apr. 1, 2005; which claims the benefit of U.S. Provisional Patent Application No. 60/559,375, filed Apr. 1, 2004, and U.S. Provisional Patent Application No. 60/587,005, filed Jul. 8, 2004. These applications are incorporated herein by reference in their entireties.

FIELD OF THE INVENTION

The field of this invention is merged compounds wherein the pharmacophores of two or more therapeutic agents are provided within a single merged compound, and more specifically to merged compounds comprising a pharmacophore of an ion channel modulating compound pharmacophore and a pharmacophore of an additional therapeutic agent such as a beta-blocker compound.

BACKGROUND OF THE INVENTION

Multiple drug therapy is a treatment and/or prevention method that may have advantages. For example, it may be used when a single therapeutic agent does not sufficiently elicit a desired biological response or when a single therapeutic agent causes a condition that requires additional treatment. Many times, two or more therapeutic agents are prescribed in tandem for the treatment or maintenance of the same physiological condition, where each therapeutic agent elicits a different or cumulative physiological response. However, multiple drug therapies are also used for the treatment or maintenance of different, yet associated, physiological conditions. For instance, a first therapeutic agent may cause a side effect which in turn requires the use of a second therapeutic agent.

Although multiple drug therapies can be beneficial treatment methods, many times they are a last-resort therapy that becomes burdensome to a patient, both in terms of lifestyle issues, such as the cost associated with taking multiple drugs, and in terms of overall patient health.

Multiple drug therapies often require a patient to take increased levels of each individual therapeutic agent to obtain the desired physiological response. The increased dosing levels in turn lead to greater physiological stress and to an increase in the risks associated with adverse side effects of each individual drug. Although therapeutic agents in multiple drug therapies are commonly intended to elicit complementary physiological responses, drug/drug interactions may be important considerations, especially at high dosing levels. Drug/drug interactions can cause serious and even detrimental side effects for a patient. For instance, competitive binding of two different drugs to the same metabolic enzymes or plasma proteins may cause a disproportionate increase in a single unbound drug substance, leading to adverse side affects and a disruption of the intended therapy.

Some of the disadvantages associated with multiple drug therapies may be overcome by incorporating the multiple pharmacophores involved in a multiple drug therapy into a single therapeutic agent. Rather than the adverse effects known to accompany high dosing levels of different therapeutic agents, the multiple pharmacophores contained within a single compound would likely have beneficial effects. For instance, synergistic effects of the multiple pharmacophores could lead to a decrease in compound dosing levels. Decreased dosing levels in turn can lead to a decrease in drug/drug interactions, a decrease in the risks associated with adverse side effects and a decrease in overall physiological stress. In addition, ease of patient care is provided, as two therapeutic agents may be simply provided in a single formulation.

Physiological conditions associated with arrhythmia often require a patient to take more than one therapeutic agent. The treatment, maintenance or prevention of conditions associated with arrhythmia could benefit from substances that combine the pharmacophore of two or more therapeutic agents into a single compound.

Cardiac ion channels are proteins that reside in the cell membrane and control the electrical activity of cardiac tissue. In response to external stimuli, such as changes in potential across the cell membrane, ion channels can form a pore through the cell membrane, and allow movement of specific ions into or out of the cell. The integrated behavior of thousands of ion channels in a single cell results in an ion current, and the integrated behavior of many ion currents makes up the characteristic cardiac action potential.

Arrhythmia is a variation from the normal rhythm of the heart beat and generally represents the end product of abnormal ion-channel structure, number or function. Both atrial arrhythmias and ventricular arrhythmias are known. The major cause of fatalities resulting from cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these cases will be first heart attacks and about 450,000 of these cases will be recurrent attacks. About one-third of the individuals experiencing these attacks will die as a result. At least 250,000 individuals a year die of coronary heart disease within 1 hour of the onset of symptoms and before they reach adequate medical aid. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., N. Engl. J. Med. 327(14):1031 Oct. 1, 1992, discussion 1031-2; Kannel and Wolf, Am. Heart J. 123(1):264-7 Jan. 1992). The prevalence of AF is likely to increase as the population ages and it is estimated that 3-5% of patients over the age of 60 years have AF (Kannel W. B., Abbot R. D., Savage D. D., McNamara P. M., N. Engl. J. Med. 306(17):1018-22, 1982; Wolf P. A., Abbot R. D., Kannel W. B. Stroke 22(8):983-8, 1991). While AF is rarely fatal, it can impair cardiac function and is a major cause of stroke (Hinton R. C., Kistler J. P., Fallon J. T., Friedlich A. L., Fisher C. M., Am. J. Cardiol. 40(4):509-13, 1977; Wolf P. A., Abbot R. D., Kannel W. B., Arch. Intern. Med. 147(9):1561-4, 1987; Wolf P. A., Abbot R. D., Kannel W. B. Stroke 22(8):983-8, 1991; Cabin H. S., Clubb K. S., Hall C., Perlmutter R. A., Feinstein A. R., Am. J. Cardiol. 65(16):1112-6, 1990).

Atrial fibrillation can be divided into three groups based on the duration of the AF episode and the refractoriness to cardioversion. The three groups are: paroxysmal, persistent and permanent, in decreasing order of receptivity to treatment. Permanent AF is resistant to any form of pharmacological treatment and cardioversion, and therefore patients with permanent AF may be considered candidates for therapies such as the MAZE procedure and can be treated with either calcium channel blockers or β-blockers to control ventricular rate.

In the remaining two categories of paroxysmal and persistent AF, treatment has a dual intent. Firstly, if a patient is in AF, physicians may wish to restore normal sinus rhythm (AF conversion). Secondly, after the patient has successfully attained normal sinus rhythm the physician will attempt to maintain normal sinus rhythm and prevent recurrence of AF.

If a patient is in AF, the physician may elect to restore sinus rhythm by the use of pharmacological rhythm control agents such as ion channel modulating compounds as described in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693, or alternatively, to allow AF to continue, and ensure that ventricular rate is controlled (correcting tachycardia-induced cardiomyopathy).

The AFFIRM (Atrial Fibrillation Follow-up Investigation in Rhythm Management, 2001) trial and RACE (Rate Control Equal to Rhythm Control) trial examined comparative efficacy and mortality rates between AF patient groups using either rhythm control or rate control drugs. Results of these studies indicated that rate and rhythm control are equivalent in efficacy in relatively asymptomatic patients with atrial fibrillation. The AFFIRM trial randomized patients to medical therapy either to restore atrial rhythm or to control ventricular heart rate, whereas RACE compared medical therapy to control heart rate with electrocardioversion of rhythm. The primary study endpoint of the AFFIRM trial, total mortality, was slightly lower in the rate-control arm, although the trend was not statistically significant. Outcomes were approximately the same for the two groups in the secondary endpoint, ischemic stroke. In the RACE study, the difference between primary endpoints was also small. It was reported that patients with hypertension in particular did not do well with electrocardioversion for rhythm control. The rate of mortality, thromboembolism, or other severe complications was approximately 19 percent for rate-control therapy vs. approximately 31 percent for rhythm control.

There are two classes of antiarrhythmic agents that restore and maintain sinus rhythm through rhythm control; Class I and Class III antiarrhythmics. A summary of their ion channel blocking profiles and mechanism of action is as follows:

Class IA: Sodium channel blockers that prolong ventricular repolarization, including quinidine, procainamide, disopyramide Class IB: Sodium channel blockers that shorten ventricular repolarization, including lidocaine, mexiletine, tocamide, phenyloin Class IC: Sodium channel blockers with little effect on ventricular repolarization, including encamide, flecamide, propafenone Class III: Potassium channel blockers that primarily prolong ventricular repolarization, including amiodarone, bretylium, d,i-sotalol, ibutilide, azimilide The SWORD study (Waldo, A L et al. Effect of d-sotalol on mortality in patients with left ventricular dysfunction after recent and remote myocardial infarction. Lancet 1996, 348, 7-12) has shown that optically pure d-sotalol increased mortality by 65% compared to placebo. In light of those results, K. Stoschitzky et al (Stoschitzky, K. et al., Racemic beta-blockers—fixed combinations of different drugs. *J. Clin. Cardiol.* 1998, 1, 14-18) suggest to replace the currently used racemic mixtures with the optically pure l-enantiomers.

There are two classes of antiarrhythmic agents that restore and maintain sinus rhythm through rate control; Class II and IV antiarrhythmics. A summary of their ion channel profiles and mechanism is as follows:

Class II: β-adrenergic blocking drugs that indirectly reduce $I_{Ca-L}$ current in SA nodes, and AV nodes, including propranolol, atenolol, metoprolol, esmolol, timolol Class IV: Calcium channel blockers that block $I_{Ca-L}$ current, thus slowing conduction in SA and AV nodes and depressing contractility in all heart myocytes, including verapamil, diltiazem The VERDICT (Verapamil versus Digoxin Cardioversion Trial, Van Noord, T. et al., VERDICT: The Verapamil versus Digoxin Cardioversion Trial: A Randomized Study on the Role of Calcium Lowering for Maintenance of Sinus Rhythm after Cardioversion of Persistent Atrial Fibrillation. *J. Cardiovasc. Electrophysiol.* 2001, 12, 766-769) has shown that the use of calcium-lowering drugs alone initiated pre-ECV (electrical cardioversion) and continued post-ECV seems to be insufficient to prevent subacute relapses.

AF patients are commonly treated with various agents, such as β-blockers, to control ventricular rate (Van Gelder, I. C. et al. A comparison of Rate Control and Rhythm Control in Patients with Recurrent Persistent Atrial Fibrillation. N. Engl. J. Med. 2002, 347 (23), 1834-1840; Basler, J. R. et al. β-Adrenergic Blockade Accelerates Conversion of Postoperative Supraventricular Tachyarrhythmias. *Anesthesiology* 1998, 89 (5), 1052-1059 and Yahalom, J. Beta-Adrenergic Blockade as Adjunctive Oral Therapy in Patients wuth Chronic Atrial Fibillation. *Chest* 1977, 71 (5), 592-596) β-adrenoceptor-blocking agents depress sinus node automaticity and inhibit atrioventricular nodal function by prolonging refractoriness and slowing conduction (Sung, R. J. et al. Beta-Adrenoceptor Blockade: Electrophysiology and Antiarrhythmic Mechanisms. *Am. Heart J.* 1984, 108, 1115-1120 and Kowey, P. R. et al. Electrophysiology of Beta Blockers in Supraventricular Arrhythmias. *Am. J. Cardiol.* 1987, 60, 32D-38D).

There remains a need in the art to identify new antiarrhythmic treatments, for both ventricular arrhythmias as well as for atrial arrhythmias. The present invention fulfills this need, and further provides other related advantages.

Related Literature

Certain ion channel modulating agents are disclosed in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693.

SUMMARY OF THE INVENTION

This invention is directed to merged compounds comprising a pharmacophore of an ion channel modulating compound and one or more pharmacophores of an additional therapeutic agent. Methods of producing the merged compounds, pharmaceutical compositions and therapeutic uses thereof are also described.

DETAILED DESCRIPTION OF THE INVENTION

As disclosed within the present invention, a variety of cardiac pathological conditions may be treated and/or prevented by the use of one or more of the merged compounds disclosed herein that, either singly or together with one or more additional therapeutic agents, are able to selectively inhibit certain combinations of cardiac ionic currents. More specifically, the cardiac currents referred to above are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The cardiac pathological conditions that may be treated and/or prevented by the compounds of the present invention may include, but are not limited to, arrhythmias such as the various types of atrial and ventricular arrhythmias.

Of particular use in the present invention are the ion channel modulating compounds disclosed in PCT Published Patent Application No. WO 1999150225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693; the disclosures of which are incorporated in full herein by reference in their entireties.

A. Definitions

In accordance with the present invention and as used herein, the following terms are defined to have the following meanings, unless explicitly stated otherwise. Terms not specifically defined herein are understood to have their common meaning.

Certain chemical groups named herein are preceded by a shorthand notation indicating the total number of carbon atoms that are to be found in the indicated chemical group. For example; $C_1$-$C_{20}$alkyl describes an alkyl group, as defined below, having a total of 1 to 20 carbon atoms, and $C_1$-$C_{20}$alkoxy describes an alkoxy group, as defined below, having a total of 1 to 20 carbon atoms. The total number of carbons in the shorthand notation does not include carbons that may exist in substituents of the group described.

"Acyl" refers to branched or unbranched hydrocarbon fragments terminated by a carbonyl —(C=O)— group containing the specified number of carbon atoms. Examples include acetyl [$CH_3$(C=O)—, a $C_2$acyl] and propionyl [$CH_3CH_2$(C=O)—, a $C_3$acyl].

"Alkanoyloxy" refers to an ester substituent wherein the ether oxygen is the point of attachment to the molecule. Examples include propanoyloxy [($CH_3CH_2$(C=O)—O—, a $C_3$alkanoyloxy] and ethanoyloxy [$CH_3$(C=O)—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl [$CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2O$(C=O)—, a $C_3$alkoxycarbonyl] and methoxycarbonyl [$CH_3O$(C=O)—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

"Modulating" in connection with the activity of an ion channel means that the activity of the ion channel may be either increased or decreased in response to administration of a compound or composition or method described herein. Thus, the ion channel may be activated, so as to transport more ions, or may be blocked, so that fewer or no ions are transported by the channel.

As used herein, a "subject" may generally be any human or non-human animal that would benefit from the methods described in this application. In one version of the methods, a subject is a human subject. In some versions of the methods, a subject is a warm-blooded animal. In some versions of the methods, a subject is a mammal. In some versions, the subject is any domestic animal, including, but not limited to dogs and cats. In some versions, the subject is any livestock animal, including but not limited to horses, pigs and cattle. In some versions, the subject is any zoo animal, including but not limited to Bengal tigers.

As used herein, unless the context makes clear otherwise, "treatment," and similar words such as "treated," "treating" etc., is an approach for obtaining beneficial or desired results, including and preferably clinical results. Treatment can involve optionally either the amelioration of symptoms of the disease or condition, or the delaying of the progression of the disease or condition.

As used herein, unless the context makes clear otherwise, "prevention," and similar words such as "prevented," "preventing" etc., is an approach for preventing the onset of a disease or condition or preventing the occurrence of the symptoms of a disease or condition, or optionally an approach for delaying the onset of a disease or condition or delaying the occurrence of the symptoms of a disease or condition. As used herein, "prevention" and similar words also includes reducing the intensity, effect, symptoms and/or burden of a disease or condition prior to onset of the disease or condition.

As used herein, an "effective amount" or a "therapeutically effective amount" of a substance is that amount sufficient to affect a desired biological effect, such as beneficial results, including clinical results.

As used herein, unless the context makes clear otherwise, "inhibition" and similar words such as "inhibit" of any ion channel means any decrease in current through that channel. When "inhibition" is used in the context of a specified concentration, it is determined by the $IC_{50}$. For example, an ion channel modulating compound which inhibits an ion channel at a concentration of 1 µM, the ion channel may be said to have an $IC_{50}$ of 1 µM for that ion channel modulating compound. This example is for illustrative purposes only and is in no way intended to be limiting.

As used herein, unless the context makes clear otherwise, "$IC_{50}$" or "$IC_{50}$ concentration" means a drug concentration at which the specified current amplitude (peak or steady-state, or integrated current) is inhibited by 50%.

As used herein, unless the context makes clear otherwise, "blocking" or "block" of an ion channel means any block or inhibition of current through that ion channel.

As used herein, unless the context makes clear otherwise, "recovery time constant of inhibition" refers to a time constant at which recovery of current amplitude occurs, presumed to reflect dissociation of a drug from its binding site, as for example, a sodium channel when the stimulus rate is decreased from 10 Hz to 1 Hz.

"Pharmaceutically acceptable carriers" for therapeutic use are well known in the pharmaceutical art, and are described, for example, in *Reminqton's Pharmaceutical Sciences*, Mack Publishing Co. (current edition). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

"Pharmaceutically acceptable salt" refers to salts of a compound of the invention derived from the combination of such compounds and an organic or inorganic acid (acid addition salts) or an organic or inorganic base (base addition salts) which retain the biological effectiveness and properties of the compounds of the present invention and which are not biologically or otherwise undesirable. The compounds of the invention described herein may be used in either the free base or salt forms, with both forms being considered as being within the scope intended herein. Pharmaceutically-acceptable salts of the compounds of the invention include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochloride and sulfates; and salts of organic acids, such as but not limited to acetates, lactates, malates, tartrates, citrates, ascorbates, succinates, butyrates, valerates and fumarates. Other examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

When the compounds described herein contain olefinic double bonds or other centers of geometric asymmetry, and unless specified otherwise, it is intended that the compounds include both E and Z geometric isomers. Likewise, all tautomeric forms are also intended to be included.

It is also to be understood that the compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

For purposes of this invention, when a bond is indicated in a formula as a wavy line, such as the bond between the oxygen atom and cyclohexyl moiety in compound of formula (IA), it is meant to indicate a bond which can give rise to either R or S stereochemistry.

Following the standard chemical literature description practice and as used herein, a full wedge bond means above the ring plane, and a dashed wedge bond means below the ring plane; one full bond and one dashed bond (i.e.,- - - - -) means a trans configuration, whereas two full bonds or two dashed bonds means a cis configuration and a wavy bond (i.e., ᴧᴧᴧ) indicates a bond that gives rise to either R or S stereochemistry.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Optically active (+) and (−), (R)- and (S)-, or (D)- and (L)-isomers may be prepared using chiral synthons or chiral reagents, or resolved using conventional techniques, such as reverse phase HPLC.

Thus, in the description of the compounds of formulae (I), (IA) and (IX) and Compound A, as described herein, all enantiomeric and diastereomeric forms of the compounds are intended. Pure stereoisomers, mixtures of enantiomers and/or diastereomers, and mixtures of different ion channel modulating compounds are described. The compounds of formulae (I), (IA) and (IX) may therefore occur as racemates, racemic mixtures and as individual diastereomers or enantiomers with all isomeric forms being included in the present invention. A racemate or racemic mixture does not imply a 50:50 mixture of stereoisomers. Where a given structural formula or chemical name is presented for a compound of formulae (I), (IA) and (IX) it is intended that all possible solvates, pharmaceutically acceptable salts, esters, amides, complexes, chelates, stereoisomers, geometric isomers, crystalline or amorphous forms, metabolites, or metabolic precursors of the compound are also separately described by the chemical structural formula or chemical name.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

The ion channel modulating compounds used in the present invention may contain an "aminocycloalkyl ether moiety", i.e., the following moiety:

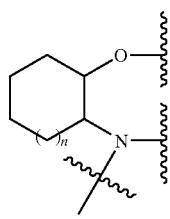

where n is 0, 1, 2, or 3. As used herein, the term "aminocycloalkyl ether moiety" includes compounds wherein the cycloalkyl group is a cyclohexyl group, such as in compounds of formula (I), formula (IA) and Compound A disclosed herein, and includes compounds wherein the cycloalkyl group is a cyclopentyl, cycloheptyl or cyclooctyl group, such as in compounds of formula (IX) disclosed herein.

As used herein, "equivalently inhibits" and "equivalently inhibited" means equally inhibits or equally inhibited. In one version, equivalently inhibits means that there is no statistically significant difference in inhibition of currents resulting from application of an ion channel modulating compound. For example, the early and sustained sodium currents are equivalently inhibited if there is no statistically significant difference in the effect of an ion channel modulating compound on early and sustained sodium currents.

As used herein, "rapidly associated and dissociated" means that a compound has blocking and unblocking kinetics of the "fast-on, fast-off" form such as the "fast-on, fast-off" kinetics defined by Carmeliet and Mubagwa (Prog. Biophys. Molec. Biol. 70, 1-72, 1998). For example, an ion channel modulating compound rapidly associates and dissociates from sodium channels where the ion channel modulating compound has 'fast-on, fast-off' kinetics as defined by Carmeliet and Mubagwa.

As used herein, "rate-independent and use-independent" inhibition means inhibition that is predominantly heart rate and/or stimulus rate and use-independent such that there is no statistically significant effect of steady-state or transient changes in heart rate or stimulus rate with respect to the inhibition. For example, an ion channel modulating compound that inhibits Kv1 channels in a "rate-independent and use-independent" manner means that there is no influence of the heart rate or stimulus rate on the amount of inhibition produced by the ion channel modulating compound on Kv1 channels.

As used herein, "affects atrial repolarizing currents" means "has a statistically significant effect on atrial repolarizing current amplitudes."

As used herein, "prolongs atrial refractoriness" means "has a statistically significant prolonging effect on atrial refractoriness."

As used herein, "has substantially no effect on ventricular tissue" means "has no statistically significant effect on normal human ventricular action potential duration or refractoriness." Any apparent difference in effect, therefore, is attributed to intrinsic variability, such as in one aspect, less than a 10% difference.

As used herein, "does not substantially slow conduction" means "has no statistically significant effect on slowing conduction in the ventricles." As such, any apparent difference in effect, therefore, is attributed to intrinsic variability. In one aspect, the ion channel modulating compound has no statistically significant effect on the slowing of conduction wherein the compound produces less than a 15%, preferably less than a 10%, increase in cardiac QRS duration at physiological heart rates.

As used herein, "rate-dependent inhibition" of an ion channel means that the level of inhibition of the ion channel changes with the frequency of stimulation.

The term "QT interval" is used as is known in the art; for example, the QT interval as measured from an electrocardiogram. As used herein, unless the context makes clear otherwise, the term "prolongs" or "prolong" generally means extends or lengthens as in duration.

The term "antiarrhythmic" is used as is known in the art; for example, as a compound which prevents or alleviates irregularities in heart rate.

The term "induces" as used herein, unless the context indicates otherwise, generally means to stimulate the occurrence of.

The term "chemically induced" or "chemically induces" is used as is known in the art. As used herein, unless the context makes clear otherwise, the term "terminating" or "terminates" generally means to bring to an end or to halt.

B. Pharmacophores in General

Rather than using multiple drugs and the problems associated with such dosage regimens, the present invention describes merged compounds that contain the pharmacophores from two or more therapeutic agents within a single compound. The term "pharmocophore", as used herein, is given its generally accepted definition of "a set of structural features in a molecule that is recognized at a receptor site and is responsible for that molecule's biological activity" (see, Gund, P:, *Prog. Mol. Subcell. Bio.,* 1977, 5:117-143). In the merged compounds of the present invention, at least one of the pharmacophores present is derived from a therapeutic agent that is an ion channel modulating compound. A compound that increases or decreases ion channel activity is said to be an ion channel modulating compound. The present invention also describes methods for preparing merged compounds comprising the pharmacophore of an ion channel modulating compound and a pharmacophore of an additional therapeutic agent, and pharmaceutical compositions comprising the merged ion channel modulating compounds.

In general, the pharmacophore of an ion channel modulating compound and a pharmacophore of an additional therapeutic agent are merged into a single compound (a "merged compound" of the invention). The pharmacophores of a merged compound may be of the same or different chemical class. That is, the pharmacophores may be from ion channel modulating compounds, or the pharmacophore of the additional therapeutic agent may be derived from an additional therapeutic agent that does not exhibit ion channel modulating activity. If more than one pharmacophore from more than one additional therapeutic agent is merged with the core skeletal structure of the ion channel modulating compound, the pharmacophores may be from the same chemical class, different chemical classes or may be a mixture of the same and different chemical classes.

In one version, the antiarrhythmic activity pharmacophore of an ion channel modulating AF drug is combined with the pharmacophore of a $\beta_1$-blocker in a single drug molecule. As an illustrative example, such an agent may be derived by merging metoprolol (LogD$_{pH7.4}$=−0.60 (Pallas 2.1), a $\beta_1$-selective antagonist (cardioselective), to the core skeletal structural of (1R,2R)/(1S,2S)-2-[(3R)-hydroxypyrrolidinyl]-1-(3,4-dimethoxyphenethoxy)cyclohexane monohydrochloride (LogD$_{pH7.4}$=1.87 (Pallas 2.1), as depicted in FIG. 1 (Compound (XXVII), LogD$_{pH7.4}$=−0.97, Pallas 2.1).

The modification of an ion channel modulating core skeletal structure may take place by the merger of a pharmacophore of an additional therapeutic agent at the carbon based structure or at any non-carbon substituent that is present on the core skeletal structure. The pharmacophore that is merged with the ion channel modulating core skeletal structure may be the entire additional therapeutic agent, the pharmacophore of the additional therapeutic agent or any portion of the additional therapeutic agent that includes the pharmacophore.

The pharmacophore of the additional therapeutic agent may be imbedded, appended or otherwise attached to the core skeletal structure of the ion channel modulating compound such that a merged ion channel modulating compound is provided. As used herein, the term "merged" will include all ways by which the additional therapeutic agent is imbedded, appended or otherwise attached to the core skeletal structure of the ion channel modulating compound.

If an additional therapeutic agent is imbedded into the core skeletal structure of the ion channel modulating compound, the additional therapeutic agent shares at least one common structural feature with the ion channel modulating compound. To be imbedded, at least a portion of that common structural feature should be present as a shared feature between the additional therapeutic agent and the core skeletal structure of the ion channel modulating compound. An additional therapeutic agent may have its common structural feature fully or partially imbedded into the core skeletal structure of the ion channel modulating compound. A schematic representation of a fully and partially imbedded common structural feature of an additional therapeutic agent is provided below wherein the common structural feature is depicted as a shaded region.

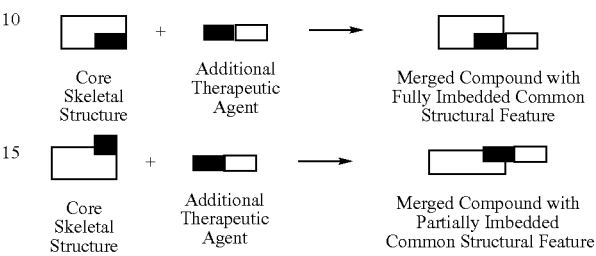

The pharmacophore of the additional therapeutic agent may be present in the merged compound by the merger of the entire additional therapeutic agent, the pharmacophore of the additional therapeutic agent, or any portion of the additional therapeutic agent that includes the pharmacophore of the additional therapeutic agent.

Generally, a merged ion channel modulating compound is described herein, wherein the merged ion channel modulating compound comprises an ion channel modulating core skeletal structure and a pharmacophore of an additional therapeutic agent. A feature of the merged ion channel modulating compound may be that the core skeletal structure of an ion channel modulating compound is modified by the merger of a pharmacophore of an additional therapeutic agent. The additional therapeutic agent may be any compound, including an ion channel modulating compound. The additional therapeutic agent may generally be of any compound class or exhibit any biological activity. Typically, the pharmacophore of the additional therapeutic agent is a pharmacophore of a compound that is used in a multiple drug therapy with an ion channel modulating compound, i.e., it is a compound that is commonly prescribed to a patient in tandem with an ion channel modulating compound. Examples of compound classes that are typically prescribed in a multiple drug therapy regimen with ion channel modulating compounds include but are not limited to anticoagulants, beta-blockers and ACE-inhibitors.

C. Additional Therapeutic Agents

Typically, the additional therapeutic agent is an ion channel modulating compound such that the merged ion channel modulating compound comprises an ion channel modulating core skeletal structure from a first ion channel modulating compound and a pharmacophore of a second ion channel modulating compound. In such an instance, the merged ion channel modulating compound comprises two ion channel pharmacophores, one from the first ion channel modulating compound and one from the second ion channel modulating compound. In some instances the additional therapeutic agent is a beta-blocker. The beta-blocker may be a beta-blocker exhibiting $\beta_1$-blocking activity. The pharmacophore from the additional therapeutic agent may be from any additional therapeutic agent, including but not limited to: an ion channel modulating compound, a beta-blocker, a beta blocker exhibiting $\beta_1$-blocking activity, antianginals, other cardiovascular agents, ACE inhibitors, antihypertensives, diuretics, antipsychotics, anticoagulants (antiplatelets), antidepressants, inotropes, Ca sensitizers, calcium channel blockers, adrenergic blocking agents, angiotensin II receptor antagonists, xanthine oxidase inhibitors (XOIs), natriuretic peptides, metabolic modulators, lipid/cholesterol modulating agents, anti-inflammatory agents, vasodilators, anti-convulsants, antioxidants, antilipids, digitalis glycosides, rate control drugs, antihistamines, antispasmodics, antibiotics, antirejection drugs, immunomodulators, chemotherapeutics, and antiarrhythmics.

When the pharmacophore from the additional therapeutic agent is a beta blocker, the beta blocker may be any beta blocker, including but not limited to: Acebutolol (Acebutolol Hydrocholoride, Sectral), Atenolol (Tenormin, Tenoretic), Betaxolol (Kerlone), Bisoprolol (Zebeta, Ziac), Cartelol (Cartrol), Carvedilol (Coreg), Esmolol (Brevibloc), Labetolol (Normodyne, Trandate, Labetolol HCL), Metoprolol (Lopressor, Lopressor HCT, Toprol, Toprol XL), Nadolol (Corgard, Corzide), Bendroflumethiazide (Corzide), Triamterene (Dyazide), Hydrochlorothiazide (Dyazide), Penbutolol (Levatol, Penbutolol Sulfate), Pindolol (Visken), Propranolol (Inderal, Inderide, Innopran, Betchron, Propanolol), Sotalol (Betapace, Sotalol), Timolol (Blocadren, Timolide, Timoptic), Oxprenolol, Moprolol, Carazolol, Alprenolol, Bunolol, Practolol, Celiprolol, Metipranolol, Mepindolol, Cetamolol, Bevantolol. This list is not exhaustive, and additional beta blockers known in the art are also contemplated.

Thus, in one aspect, the pharmacophore from the additional therapeutic agent is derived from a compound with β-blocking activity. A drug or a pharmacophore with β-blocking activity is said to be a "beta-blocker". The merged ion channel modulating compounds may be used for the prevention of atrial fibrillation, ventricular rate control, or the like. In another aspect, the pharmacophore from the additional therapeutic agent is derived from a compound with β1-blocking activity. A compound or a pharmacophore with β1-blocking activity is said to be a "cardioselective beta-blocker". In a preferred aspect, the β1-blocker moiety may have the S configuration (Stoschitzki, K. et al., Racemic beta-blockers—fixed combinations of different drugs. *J. Clin. Cardiol.* 1998, 1, 14-18.

D. Ion Channel Modulating Compounds

In one aspect, the merged compounds of the invention comprise a pharmacophore of an ion channel modulating compound and a pharmacophore of a beta blocker compound. Generally, any compound that modulates ion channel activity may by an ion channel modulating compound. A compound that modulates ion channel activity may be a compound that increases or decreases ion channel activity. An ion channel modulating compound that decreases ion channel activity may be a compound that blocks ion channel activity completely or partially.

In another version, any compound that either singly or together with one or more additional compounds selectively inhibit certain combinations of cardiac ionic currents is an ion channel modulating compound. The cardiac currents may be the sodium currents and early repolarizing currents. Ion channel modulating compounds may block cardiac currents from extracellular loci. Such compounds act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias. An ion channel modulating compound may selectively inhibit cardiac early repolarizing currents and cardiac sodium currents. Ion channel modulating compounds may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation. An ion channel modulating compound may be an atrial selective agent. An ion channel modulating compound may treat or prevent ventricular arrhythmia. An ion channel modulating compound may block cardiac sodium currents or cardiac early repolarizing currents. An ion channel modulating compound may inhibit multiple cardiac ionic currents. An ion channel modulating compound may be used to treat or prevent arrhythmic, including ventricular or atrial arrhythmia, particularly atrial fibrillation.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular loci in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972). For ion channel modulating compounds with the specific ranges of pKa described above, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increase in cardiac milieu acidity.

Particular ion channel modulating compounds have structural characteristics that may be determined by various physical methods, such as single crystal X-ray crystallography. For instance, some ion channel modulating compounds comprise a cycloalkane ring and substituents J and K as shown below in structure T, wherein the relative positions of J and K provide a "C" shaped angle and wherein n=1, 2, 3 or 4.

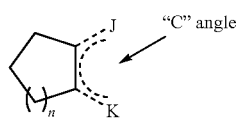

(T)

Typically, one of J and K comprises a hydrophobic moiety, such as but not limited to a moiety comprising alkyl and/or aryl moieties. In one variation, one of J and K comprises a hydrophobic aromatic moiety, which may be attached to the cycloalkane ring of structure T via an ether bond. Typically, one of J and K comprises a hydrophilic moiety, such as a heteroatom containing moiety, including but not limited to a nitrogen containing moiety that is available to form a quaternary salt and/or a hydroxyl moiety. In one variation, one of J and K comprises a nitrogen containing moiety substituted with a hydroxyl moiety or the like, such as a pyrrolidinyl moiety. In a particular variation of structure T, n=2, J comprises an aromatic moiety and K comprises a nitrogen containing moiety substituted with a hydroxyl moiety or the like. The cycloalkane ring may be optionally substituted. In one version, the cycloalkane ring may be replaced by a structural moiety imparting rigidity to the relative positions of the J and K groups. For example if the J and K groups are attached to atoms L and M that are directly bonded to each other, any group that does not allow substantial rotation about the bond between atoms L and M can impart rigidity to the relative positions of the J and K groups. For example, the ion channel modulating compound may be a compound of formula

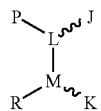

where J and K are as described above and groups P and R are moieties such that there is not substantial rotation about the L-M bond. In one example P and R are taken together form a cyclic moiety that prevents substantial rotation about the L-M bond.

In one version, the ion channel modulating compound comprises an amino substituted 5, 6, 7 or 8-membered ring, which may be a 5, 6, 7, or 8-membered substituted or unsubstituted cycloalkyl ring. The amino substituted cycloalkane ring may be an aminocyclohexyl ring and may be further substituted with one or more additional moieties. In one version, the amino substituted cycloalkane ring is further substituted with an ether moiety. In some instances, the ion channel modulating compound comprises an aminocyclohexyl ring that is further substituted with an ether moiety.

In another, the ion channel modulating compound is a protonated version of any of the ion channel modulating compounds described herein. That is, for each ion channel modulating compound described herein, the quaternary protonated amine form of the compound may also be considered as an amino ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Of particular interest to the present invention are the ion channel modulating compounds disclosed in PCT Published Patent Application No. WO 1999150225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693; the disclosures of which are incorporated in full herein by reference in their entireties. The ion channel modulating compounds disclosed therein may be used in preparing the merged compounds of the invention.

Accordingly, one embodiment of this invention utilizes the ion channel modulating compounds of formula (I), or solvates or pharmaceutically acceptable salts thereof:

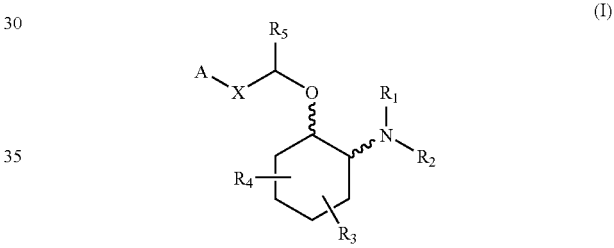

(I)

wherein, independently at each occurrence,

X is selected from a direct bond, —C(R$_6$, R$_{14}$)—Y— and —C(R$_{13}$)=CH—, with the proviso that when X is a direct bond and A is formula (III), then at least one of R$_7$, R$_8$ and R$_9$ is not hydrogen;

Y is selected from a direct bond, O, S and C$_1$-C$_4$alkylene;

R$_{13}$ is selected from hydrogen, C$_1$-C$_6$alkyl, C$_3$-C$_8$cycloalkyl, aryl and benzyl;

R$_1$ and R$_2$ are independently selected from hydrogen, C$_1$-C$_8$alkyl, C$_3$-C$_8$alkoxyalkyl, C$_1$-C$_8$hydroxyalkyl, and C$_7$-C$_{12}$aralkyl; or R$_1$ and R$_2$, when taken together with the nitrogen atom to which they are directly attached in formula (I), form a ring denoted by formula (II):

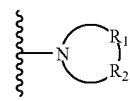

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_6$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

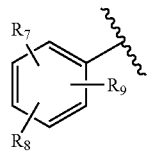
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$, $R_{16}$) where $R_{15}$ and $R_{16}$ are independently selected from hydrogen, acetyl, methanesulfonyl and $C_1$-$C_6$alkyl;

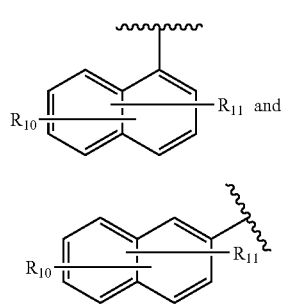
(IV) and
(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$, $R_{16}$) where $R_{15}$ and $R_{16}$ are independently selected from hydrogen, acetyl, methanesulfonyl, and $C_1$-$C_6$alkyl;

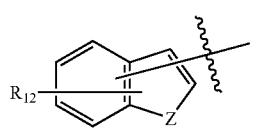
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$, $R_{16}$) where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

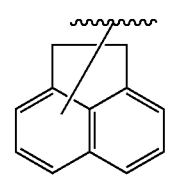
(VII)

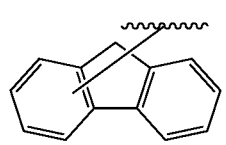
(VIII)

as isolated enantiomeric, diastereomeric and geometric isomers thereof, and mixtures thereof.

Of particular use to this invention are compounds of formula (I) selected from the group consisting of the following:
(1R,2R)/(1S,2S)-[2-(4-morpholinyl)-1-(2-naphthenethoxy)]cyclohexane;
(1R,2R)/(1S,2S)-[2-(4-morpholinyl)-1-(1-naphthenethoxy)]cyclohexane;
(1R,2R)/(1S,2S)-[2-(4-morpholinyl)-1-(4-bromophenethoxy)]cyclohexane;
(1R,2R)/(1S,2S)-[2-(4-morpholinyl)-1-[2-(2-naphthoxy)ethoxy]]cyclohexane;
(1R,2R)/(1S,2S)-[2-(4-morpholinyl)-1-[2-(4-bromophenoxy)ethoxy]]cyclohexane;
(1R,2R)/(1S,2S)-[2-(4-morpholinyl)-1-(3,4-dimethoxyphenethoxy)]cyclohexane;
(1R,2R)/(1S,2S)-[2-(1-pyrrolidinyl)-1-(1-naphthenethoxy)]cyclohexane;
(1R,2R)/(1S,2S)-[2-(4-morpholinyl)-1-(2-(benzo[b]thiophen-3-yl)]cyclohexane;
(1R,2R)/(1S,2S)-[2-(4-morpholinyl)-1-(2-(benzo[b]thiophen-4-yl)]cyclohexane;
(1R,2R)/(1S,2S)-[2-(4-morpholinyl)-1-(3-bromophenethoxy)]cyclohexane;
(1R,2R)/(1S,2S)-[2-(4-morpholinyl)-1-(2-bromophenethoxy)]cyclohexane;
(1R,2R)/(1S,2S)-[2-(4-morpholinyl)-1-(3-(3,4-dimethoxyphenyl)propoxy)]cyclohexane;

(1R,2R)/(1S,2S)-[2-[bis(2-methoxyethyl)aminyl]-1-(2-naphthenethoxy)]cyclohexane;

(1R,2R)/(1S,2S)-2-(4-morpholinyl)-1-(3,4-dichlorophenethoxy)cyclohexane;

(1R,2R)/(1S,2S)-2-(3-ketopyrrolidinyl)-1-(1-naphthenethoxy)cyclohexane;

(1R,2R)/(1S,2S)-2-(1-acetylpiperazinyl)-1-(2-naphthenethoxy)cyclohexane;

(1R,2R)/(1S,2S)-2-(3-ketopyrrolidinyl)-1-(2,6-dichlorophenethoxy)cyclohexane;

(1R,2R)/(1S,2S)-2-[1,4-dioxa-7-azaspiro[4.4]non-7-yl]-1-(1-naphthenethoxy)cyclohexane;

(1R,2S)/(1S,2R)-2-(4-morpholinyl)-1-[(2-trifluoromethyl)phenethoxy]cyclohexane monohydrochloride;

(1R,2R)/(1S,2S)-2-(3-ketopyrrolidinyl)-1-[3-(cyclohexyl)propoxy]cyclohexane monohydrochloride;

(1R,2R)/(1S,2S)-2-(3-acetoxypyrrolidinyl)-1-(1-naphthenethoxy)cyclohexane monohydrochloride;

(1R,2R)/(1S,2S)-2-(4-morpholinyl)-1-[(2,6-dichlorophenyl)methoxy]cyclohexane monohydrochloride;

(1R,2R)/(1S,2S)-2-(3-ketopyrrolidinyl)-1-[(2,6-dichlorophenyl)methoxy]cyclohexane monohydrochloride;

(1R,2R)/(1S,2S)-2-(3-hydroxypyrrolidinyl)-1-(2,6-dichlorophenethoxy)cyclohexane monohydrochloride;

(1R,2R)/(1S,2S)-2-(3-ketopyrrolidinyl)-1-(2,2-diphenylethoxy)cyclohexane monohydrochloride;

(1R,2R)/(1S,2S)-2-(3-thiazolidinyl)-1-(2,6-dichlorophenethoxy)cyclohexane monohydrochloride;

(1R,2S)/(1S,2R)-2-(3-ketopyrrolidinyl)-1-(1-naphthenethoxy)cyclohexane monohydrochloride; and (1R,2R)/(1S,2S)-2-(3-hydroxypyrrolidinyl)-1-(3,4-dimethoxyphenethoxy)cyclohexane monohydrochloride.

Another embodiment of this invention utilizes the ion channel modulating compounds of formula (XV), or solvates or pharmaceutically acceptable salts thereof:

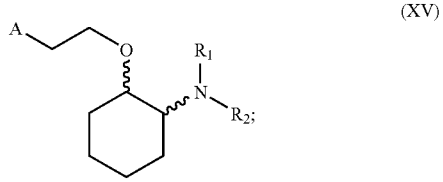

(XV)

wherein, independently at each occurrence, $R_1$ and $R_2$ are defined as above for compounds of formula (I); and A is selected from any of formulae (III), (IV), (V) and (VI) as defined above for compounds of formula (I), wherein $R_7$, $R_{10}$, $R_{11}$, and $R_{12}$, are hydrogen, $R_8$ and $R_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and $NH_2$, with the proviso that at least one of $R_8$ and $R_9$ is not hydrogen; and Z is selected from O and S.

Another embodiment of this invention utilizes the ion channel modulating compounds of formula (IA), or solvates, pharmaceutically acceptable salts, esters, amides, complexes, chelates, stereoisomers, stereoisomeric mixtures, geometric isomers, crystalline or amorphous forms, metabolites, or metabolic precursors thereof:

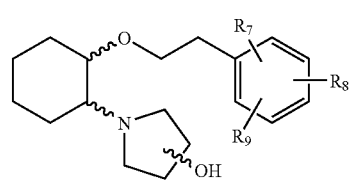

(IA)

wherein, $R_7$, $R_8$ and $R_9$ are independently selected from hydrogen, hydroxy and $C_1$-$C_6$alkoxy, as isolated enantiomeric, diastereomeric and geometric isomers thereof, and mixtures thereof, with the proviso that $R_7$, $R_8$ and $R_9$ cannot all be hydrogen.

Of particular use to this invention are compounds of formula (IA) selected from the group consisting of the following:

(1R,2R)/(1S,2S)-2-[(3R)/(3S)-hydroxypyrrolidinyl]-1-(3,4-dimethoxyphenethoxy)-cyclohexane;

(1R,2R)/(1S,2S)-2-[(3R)-hydroxypyrrolidinyl]-1-(3,4-dimethoxyphenethoxy)-cyclohexane;

(1R,2R)/(1S,2S)-2-[(3S)-hydroxypyrrolidinyl]-1-(3,4-dimethoxyphenethoxy)-cyclohexane;

(1R,2R)-2-[(3R)hydroxypyrrolidinyl]-1-(3,4-dimethoxyphenethoxy)-cyclohexane;

(1R,2R)-2-[(3S)-hydroxypyrrolidinyl]-1-(3,4-dimethoxyphenethoxy)-cyclohexane;

(1R,2S)-2-[(3R)-hydroxypyrrolidinyl]-1-(3,4-dimethoxyphenethoxy)-cyclohexane;

(1R,2S)-2-[(3S)-hydroxypyrrolidinyl]-1-(3,4-dimethoxyphenethoxy)-cyclohexane;

(1S,2R)-2-[(3R)-hydroxypyrrolidinyl]-1-(3,4-dimethoxyphenethoxy)-cyclohexane;

(1S,2R)-2-[(3S)-hydroxypyrrolidinyl]-1-(3,4-dimethoxyphenethoxy)-cyclohexane;

(1S,2S)-2-[(3R)-hydroxypyrrolidinyl]-1-(3,4-dimethoxyphenethoxy)-cyclohexane;

(1S,2S)-2-[(3S)-hydroxypyrrolidinyl]-1-(3,4-dimethoxyphenethoxy)-cyclohexane; and (1R,2S)/(1S,2R)-2-[(3R)/(3S)-hydroxypyrrolidinyl]-1-(3,4-dimethoxyphenethoxy)-cyclohexane.

Another embodiment of this invention utilizes the ion channel modulating compounds of formula (IX), or solvates or pharmaceutically acceptable salts thereof:

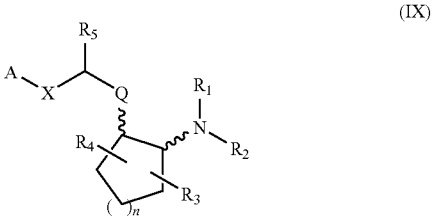

(IX)

wherein, independently at each occurrence, n is selected from 1, 3 and 4;

Q is either 0 (oxygen) or —O—C(O);

X is selected from a direct bond, —C($R_6$, $R_{14}$)—Y—, and —C($R_{13}$)=CH—;

Y is selected from a direct bond, O, S, and $C_1$-$C_4$alkylene;

$R_{13}$ is selected from hydrogen, $C_1$-$C_6$alkyl, $C_3$-$C_8$cycloalkyl, aryl, and benzyl;

$R_1$ and $R_2$ are independently selected from hydrogen, $C_1$-$C_8$alkyl, $C_3$-$C_8$alkoxyalkyl, $C_{1-8}$hydroxyalkyl, and $C_7$-$C_{12}$aralkyl; or $R_1$ and $R_2$, when taken together with the nitrogen atom to which they are directly attached in formula (IX), form a ring denoted by formula (II):

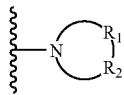

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (IX), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (IX) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

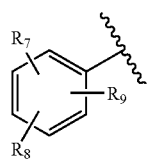

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$, $R_{16}$) where $R_{15}$ and $R_{16}$ are independently selected from hydrogen, acetyl, methanesulfonyl and $C_1$-$C_6$alkyl;

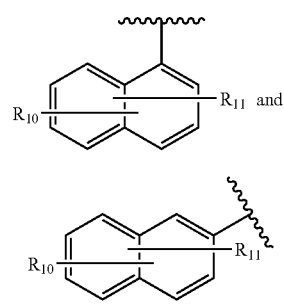

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$, $R_{16}$) where $R_{15}$ and $R_{16}$ are independently selected from hydrogen, acetyl, methanesulfonyl, and $C_1$-$C_6$alkyl;

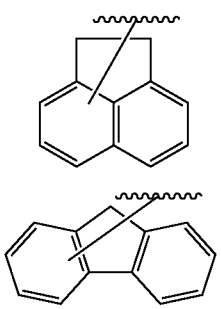

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$, $R_{16}$) where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (IX) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

(VII)

(VIII)

as isolated enantiomeric, diastereomeric and geometric isomers thereof, and mixtures thereof.

Of particular use in this invention are the ion channel modulating compounds of formula (IX) selected from the group consisting of the following:

(1R,2R)/(1S,2S)-2-(4-morpholinyl)-1-(2-naphthalenethoxy)cyclopentane monohydrochloride; and (1R,2R)/(1S,2S)-2-(3-ketopyrrolidinyl)-1-(2,6-dichlorophenethoxy)cyclopentane monohydrochloride.

Another embodiment of this invention uses an ion channel modulating compound of formula (IA) having the following formula:

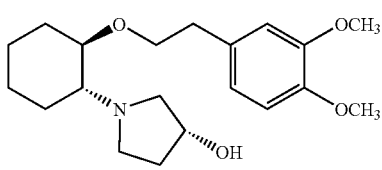

or pharmaceutically acceptable salts or solvates thereof.

This compound has the chemical name of (1R,2R)-2-[(3R)-hydroxypyrrolidinyl]-1-(3,4-dimethoxyphenethoxy)cyclohexane and is referred to herein as "Compound A". For purposes of this invention, the term "Compound A" is intended to include this compound and its pharmaceutically acceptable salts, solvates, esters, amides, complexes, chelates, stereoisomers, stereoisomeric mixtures, geometric isomers, crystalline or amorphous forms, metabolites, or metabolic precursors thereof.

Another embodiment of this invention utilizes an ion channel modulating compound of formula (IXXX):

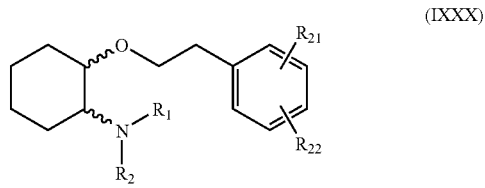

(IXXX)

wherein $\sim\sim\sim$ indicates a bond that gives rise to either R or S stereochemistry;

wherein $R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or wherein $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in the formula above to form a ring denoted by formula (II):

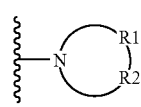

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five or six membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in the formula (IXXX) above to form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptane-3-yl; and $R_{21}$ and $R_{22}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$, $R_{16}$) where $R_{15}$ and $R_{16}$ are independently selected from hydrogen, acetyl, methanesulfonyl and $C_1$-$C_6$alkyl; and as isolated enantiomeric, diastereomeric and geometric isomers thereof, and mixtures thereof.

In another embodiment of the invention, any ion channel modulating compound described above is a protonated version of any of the ion channel modulating compounds described herein. That is, for each ion channel modulating compound described herein, the quaternary protonated amine forms of the compound may also be considered as an ion channel modulating compounds. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

E. Merged Compounds of the Invention

In one embodiment, the merged ion channel modulating compounds are compounds of formula (IXXXa)

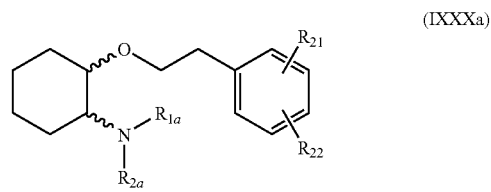

(IXXXa)

wherein:

$\sim\sim\sim$ indicates a bond that gives rise to either R or S stereochemistry;

$R_{1a}$ and $R_{2a}$ are each individually a hydrogen, an aryloxypropanolamine side chain of a $\beta_1$-blocker or a substituted or unsubstituted propanol-3-yl, wherein the substituted propanol-3-yl is substituted at one or more position with a group selected from hydroxyl, phenyl, or substituted phenyl wherein the substituted phenyl is substituted with $C_1$-$C_8$ alkyloxylalkyl group; or $R_{1a}$ and $R_{2a}$ are taken together with the nitrogen atom to which they are attached to form a 5 to 8-membered heterocyclic ring that is optionally substituted with a group selected from a hydroxyl, an amino or substituted amino, an alkoxy or substituted alkoxy group;

$R_{21}$ and $R_{22}$ are independently selected from a substituted or unsubstituted $C_1$-$C_8$ alkoxy group wherein the substituted $C_1$-$C_8$ alkoxy is substituted with a hydroxyl and/or a substituted or unsubstituted amino group; and as isolated enantiomeric, diastereomeric and geometric isomers thereof, and mixtures thereof.

Of particular interest are those compounds of formula (IXXXa) wherein $R_{1a}$, $R_{2a}$, $R_{21}$ and/or $R_{22}$ moieties are selected from the substituents listed in Table 1 in any combination of moieties listed in Table 1.

TABLE 1

Formula (IXXXa) substituents of merged ion channel modulating compounds.

| Row | $R_{1a}$ | $R_{2a}$ | $R_{21}$ | $R_{22}$ |
|---|---|---|---|---|
| A | (structure) | H | OMe | OMe |
| B | (structure) | | OMe | (structure) |
| C | (structure) | | OMe | OMe |
| D | (structure) | | OMe | OMe |

An example of a compound of formula (IXXXa) in Row A in Table 1 is as follows:

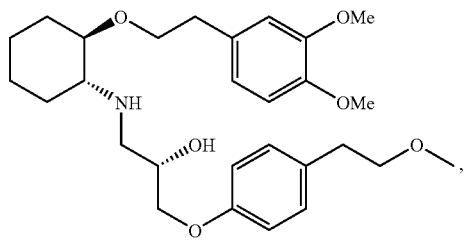

i.e., (S)-1-((1R,2R)-2-(3,4-dimethoxyphenethoxy)cyclohexylamino)-3-(4-(2-methoxyethyl)phenoxy)propan-2-ol; as well as the following isomers:
(R)-1-((1R,2R)-2-(3,4-dimethoxyphenethoxy)cyclohexylamino)-3-(4-(2-methoxyethyl)phenoxy)propan-2-ol;
(S)-1-((1S,2S)-2-(3,4-dimethoxyphenethoxy)cyclohexylamino)-3-(4-(2-methoxyethyl)phenoxy)propan-2-ol;
(R)-1-((1S,2S)-2-(3,4-dimethoxyphenethoxy)cyclohexylamino)-3-(4-(2-methoxyethyl)phenoxy)propan-2-ol;
(S)-1-((1S,2R)-2-(3,4-dimethoxyphenethoxy)cyclohexylamino)-3-(4-(2-methoxyethyl)phenoxy)propan-2-ol;
(R)-1-((1S,2R)-2-(3,4-dimethoxyphenethoxy)cyclohexylamino)-3-(4-(2-methoxyethyl)phenoxy)propan-2-ol;
(S)-1-((1R,2S)-2-(3,4-dimethoxyphenethoxy)cyclohexylamino)-3-(4-(2-methoxyethyl)phenoxy)propan-2-ol;
(R)-1-((1R,2S)-2-(3,4-dimethoxyphenethoxy)cyclohexylamino)-3-(4-(2-methoxyethyl)phenoxy)propan-2-ol.

An example of a compound of formula (IXXXa) in Row B in Table 1 is as follows:

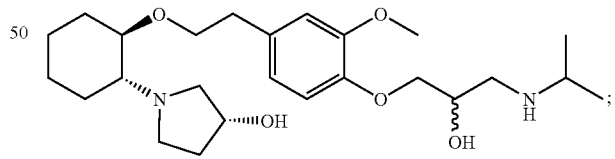

(R)-1-((1R,2R)-2-(4-(2-hydroxy-3-(isopropylamino)propoxy)-3-methoxyphenethoxy)cyclohexyl)pyrrolidin-3-ol; as well as the following isomers:
(S)-1-((1R,2R)-2-(4-(2-hydroxy-3-(isopropylamino)propoxy)-3-methoxyphenethoxy)cyclohexyl)pyrrolidin-3-ol;
(R)-1-((1S,2S)-2-(4-(2-hydroxy-3-(isopropylamino)propoxy)-3-methoxyphenethoxy)cyclohexyl)pyrrolidin-3-ol;
(S)-1-((1S,2S)-2-(4-(2-hydroxy-3-(isopropylamino)propoxy)-3-methoxyphenethoxy)cyclohexyl)pyrrolidin-3-ol;
(R)-1-((1S,2R)-2-(4-(2-hydroxy-3-(isopropylamino)propoxy)-3-methoxyphenethoxy)cyclohexyl)pyrrolidin-3-ol;

(S)-1-((1S,2R)-2-(4-(2-hydroxy-3-(isopropylamino)propoxy)-3-methoxyphenethoxy)cyclohexyl)pyrrolidin-3-ol;
(R)-1-((1R,2S)-2-(4-(2-hydroxy-3-(isopropylamino)propoxy)-3-methoxyphenethoxy)cyclohexyl)pyrrolidin-3-ol;
(S)-1-((1R,2S)-2-(4-(2-hydroxy-3-(isopropylamino)propoxy)-3-methoxyphenethoxy)cyclohexyl)pyrrolidin-3-ol.

Example of a compound of formula (IXXXa) in Row C in Table 1 is as follows:

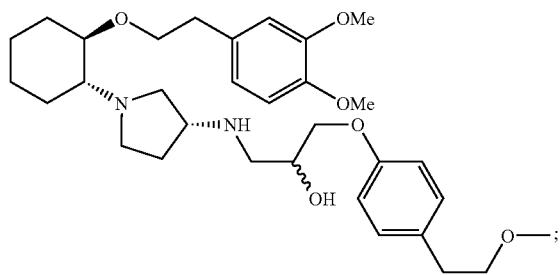

i.e., 1-((R)-1-((1R,2R)-2-(3,4-dimethoxyphenethoxy)cyclohexyl)pyrrolidin-3-ylamino)-3-(4-(2-methoxyethyl)phenoxy)propan-2-ol; as well as the following isomers:
1-((S)-1-((1R,2R)-2-(3,4-dimethoxyphenethoxy)cyclohexyl)pyrrolidin-3-ylamino)-3-(4-(2-methoxyethyl)phenoxy)propan-2-ol;
1-((R)-1-((1S,2S)-2-(3,4-dimethoxyphenethoxy)cyclohexyl)pyrrolidin-3-ylamino)-3-(4-(2-methoxyethyl)phenoxy)propan-2-ol;
1-((S)-1-((1S,2S)-2-(3,4-dimethoxyphenethoxy)cyclohexyl)pyrrolidin-3-ylamino)-3-(4-(2-methoxyethyl)phenoxy)propan-2-ol;
1-((R)-1-((1S,2R)-2-(3,4-dimethoxyphenethoxy)cyclohexyl)pyrrolidin-3-ylamino)-3-(4-(2-methoxyethyl)phenoxy)propan-2-ol;
1-((S)-1-((1S,2R)-2-(3,4-dimethoxyphenethoxy)cyclohexyl)pyrrolidin-3-ylamino)-3-(4-(2-methoxyethyl)phenoxy)propan-2-ol;
1-((R)-1-((1R,2S)-2-(3,4-dimethoxyphenethoxy)cyclohexyl)pyrrolidin-3-ylamino)-3-(4-(2-methoxyethyl)phenoxy)propan-2-ol.

Example of a compound of formula (IXXXa) in Row D in Table 1 is as follows:

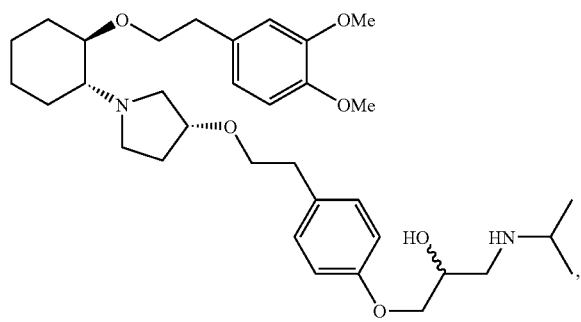

i.e., 1-(4-(2-((R)-1-((1R,2R)-2-(3,4-dimethoxyphenethoxy)cyclohexyl)pyrrolidin-3-yloxy)ethyl)phenoxy)-3-(isopropylamino)propan-2-ol; as well as the following isomers:
1-(4-(2-((S)-1-((1R,2R)-2-(3,4-dimethoxyphenethoxy)cyclohexyl)pyrrolidin-3-yloxy)ethyl)phenoxy)-3-(isopropylamino)propan-2-ol;
1-(4-(2-((R)-1-((1S,2S)-2-(3,4-dimethoxyphenethoxy)cyclohexyl)pyrrolidin-3-yloxy)ethyl)phenoxy)-3-(isopropylamino)propan-2-ol;
1-(4-(2-((S)-1-((1S,2S)-2-(3,4-dimethoxyphenethoxy)cyclohexyl)pyrrolidin-3-yloxy)ethyl)phenoxy)-3-(isopropylamino)propan-2-ol;
1-(4-(2-((R)-1-((1S,2R)-2-(3,4-dimethoxyphenethoxy)cyclohexyl)pyrrolidin-3-yloxy)ethyl)phenoxy)-3-(isopropylamino)propan-2-ol;
1-(4-(2-((S)-1-((1S,2R)-2-(3,4-dimethoxyphenethoxy)cyclohexyl)pyrrolidin-3-yloxy)ethyl)phenoxy)-3-(isopropylamino)propan-2-ol;
1-(4-(2-((R)-1-((1R,2S)-2-(3,4-dimethoxyphenethoxy)cyclohexyl)pyrrolidin-3-yloxy)ethyl)phenoxy)-3-(isopropylamino)propan-2-ol;
1-(4-(2-((S)-1-((1R,2S)-2-(3,4-dimethoxyphenethoxy)cyclohexyl)pyrrolidin-3-yloxy)ethyl)phenoxy)-3-(isopropylamino)propan-2-ol.

Examples Of Merged Ion Channel Modulating Compounds Including Metoprolol

A merged ion channel modulating compound may comprise a pharmacophore from an additional therapeutic agent that is also an ion channel modulating compound. In a particular aspect, the additional moiety is metoprolol, and the ion channel modulating compound is (1R,2R)/(1S,2S)-2-[(3R)-hydroxypyrrolidinyl]-1-(3,4-dimethoxyphenethoxy)cyclohexane or its monohydrochloride salt, such that the merged ion channel modulating compound is as shown in FIG. 1 (Compound (XXX)) and FIG. 2 (Compounds (XXXI), (XXXII), and (XXXIII)). In another variation, the additional therapeutic agent is (S)-metoprolol, and the ion channel modulating compound is (1R,2R)-2-[(3R)-hydroxypyrrolidinyl]-1-(3,4-dimethoxyphenethoxy)cyclohexane (Compound A) or its monohydrochloride (XXVII).

In this example, metoprolol was chosen as the additional therapeutic agent, and is a cardioselective β-adrenoceptor-blocking agent which is being used for the treatment of AF (Page, R. L. Beta-Blockers for Atrial Fibrillation: Must We Consider Asymptomatic Arrhythmias? *J. Am. Coll. Cardiol.* 2000, 36 (1), 147-150). However, other cardioselective β-adrenoceptor-blocking agents could be selected for the additional therapeutic agent from the pharmacopea following the type of pharmacological profile targeted (i.e. short-acting vs. long-acting, potency vs. selectivity. For example: Esmolol, Acebutolol, Practolol, Atenolol, Celiprolol, Betaxolol, Cetamolol, Bisoprolol and Bevantolol). Compound (XXX) was prepared using chemical reactions as illustrated in Scheme 1. Diastereomeric mixtures or pure enantiomeric forms of the compounds can be prepared by methods known in the art.

Compound (XXX) in FIG. 1 is one example of a merged ion channel modulating compound in which the compound is formed from the merger of (XXVII) and metoprolol.

FIG. 1. Structure of Metoprolol, Compound (XXVII) and Compound (XXX)

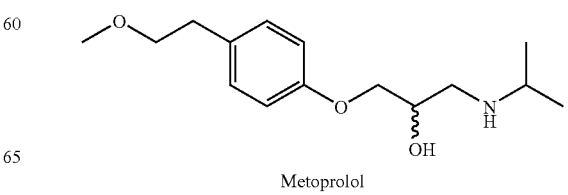

Metoprolol

-continued

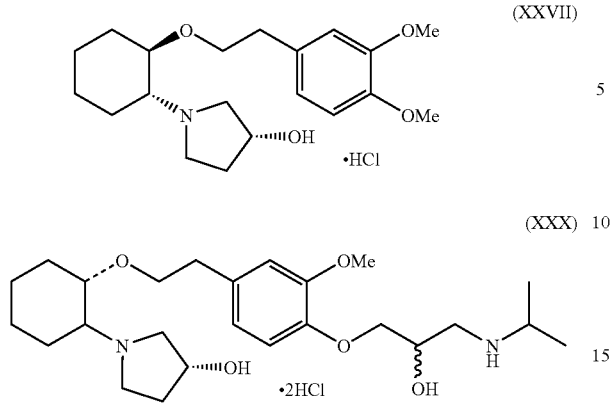

(XXVII)

(XXX)

Examples of a compound of formula (XXX) are as follows:

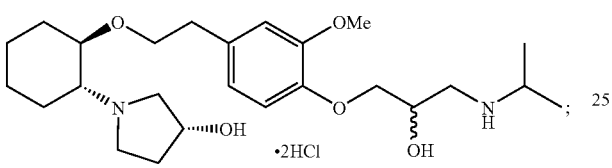

i.e., (R)-1-((1R,2R)-2-(4-(2-hydroxy-3-(isopropylamino)propoxy)-3-methoxyphenethoxy)cyclohexyl)pyrrolidin-3-ol dihydrochloride; as well as the following isomers:

(S)-1-((1R,2R)-2-(4-(2-hydroxy-3-(isopropylamino)propoxy)-3-methoxyphenethoxy)cyclohexyl)pyrrolidin-3-ol dihydrochloride;

(R)-1-((1S,2S)-2-(4-(2-hydroxy-3-(isopropylamino)propoxy)-3-methoxyphenethoxy)cyclohexyl)pyrrolidin-3-ol dihydrochloride;

(S)-1-((1S,2S)-2-(4-(2-hydroxy-3-(isopropylamino)propoxy)-3-methoxyphenethoxy)cyclohexyl)pyrrolidin-3-ol dihydrochloride;

(R)-1-((1S,2R)-2-(4-(2-hydroxy-3-(isopropylamino)propoxy)-3-methoxyphenethoxy)cyclohexyl)pyrrolidin-3-ol dihydrochloride;

(S)-1-((1S,2R)-2-(4-(2-hydroxy-3-(isopropylamino)propoxy)-3-methoxyphenethoxy)cyclohexyl)pyrrolidin-3-ol dihydrochloride;

(R)-1-((1R,2S)-2-(4-(2-hydroxy-3-(isopropylamino)propoxy)-3-methoxyphenethoxy)cyclohexyl)pyrrolidin-3-ol dihydrochloride;

(S)-1-((1R,2S)-2-(4-(2-hydroxy-3-(isopropylamino)propoxy)-3-methoxyphenethoxy)cyclohexyl)pyrrolidin-3-ol dihydrochloride.

Other such merged ion channel modulating compounds include but are not limited to Compounds (XXXI), (XXXII) and (XXXIII) depicted in FIG. 2. The propanolamine side-chain of metoprolol is either merged to the pyrrolidine ring of Compound (XXXI), (LogD$_{pH7.4}$=2.29, Pallas 2.1) or further embedded in the cyclohexane scaffold where it replaces the pyrrolidinol ring of Compound A (Compound (XXXII), LogD$_{pH7.4}$=2.59, Pallas 2.1). Metoprolol can be linked to the hydroxyl functionality of Compound A via its phenethoxy group (Compound (XXXIII), LogD$_{pH7.4}$=1.85, Pallas 2.1).

FIG. 2. Compounds (XXXI), (XXXII) and (XXXIII)

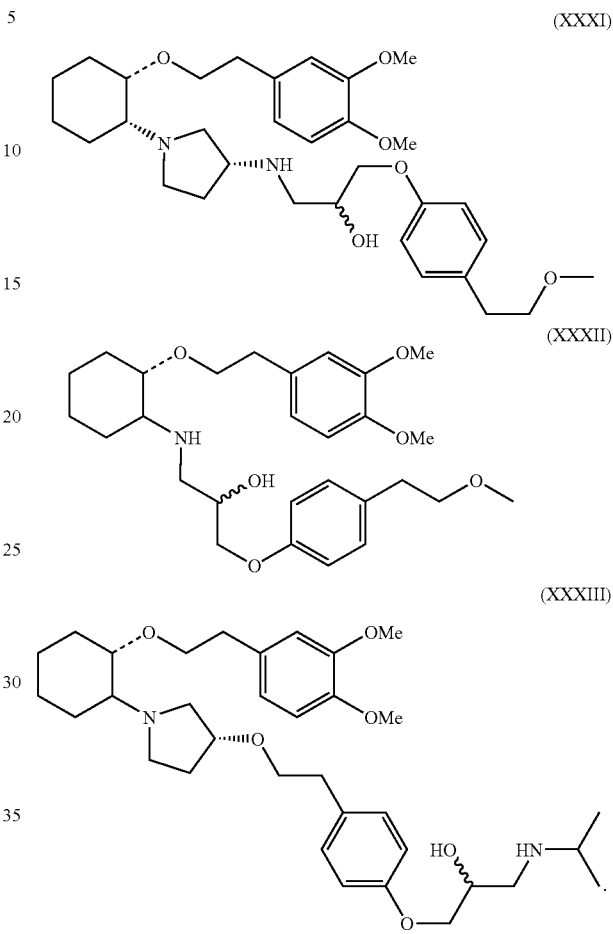

Examples of compounds of formula (XXXI) are as follows:

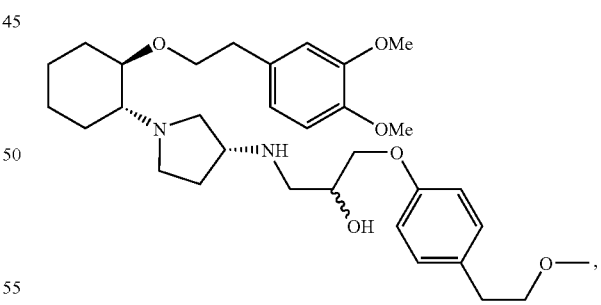

i.e., 1-((R)-1-((1R,2R)-2-(3,4-dimethoxyphenethoxy)cyclohexyl)pyrrolidin-3-ylamino)-3-(4-(2-methoxyethyl)phenoxy)propan-2-ol; as well as the following isomers:

1-((S)-1-((1R,2R-2-(3,4-dimethoxyphenethoxy)cyclohexyl)pyrrolidin-3-ylamino)-3-(4-(2-methoxyethyl)phenoxy)propan-2-ol;

1-((R)-1-((1S,2S)-2-(3,4-dimethoxyphenethoxy)cyclohexyl)pyrrolidin-3-ylamino)-3-(4-(2-methoxyethyl)phenoxy)propan-2-ol;

1-((R)-1-((1S,2R)-2-(3,4-dimethoxyphenethoxy)cyclo-
hexyl)pyrrolidin-3-ylamino)-3-(4-(2-methoxyethyl)phe-
noxy)propan-2-ol;
1-((S)-1-((1S,2R)-2-(3,4-dimethoxyphenethoxy)cyclo-
hexyl)pyrrolidin-3-ylamino)-3-(4-(2-methoxyethyl)phe-
noxy)propan-2-ol;
1-((R)-1-((1R,2S)-2-(3,4-dimethoxyphenethoxy)cyclo-
hexyl)pyrrolidin-3-ylamino)-3-(4-(2-methoxyethyl)phe-
noxy)propan-2-ol;
1-((S)-1-((1R,2S)-2-(3,4-dimethoxyphenethoxy)cyclo-
hexyl)pyrrolidin-3-ylamino)-3-(4-(2-methoxyethyl)phe-
noxy)propan-2-ol.

Examples of compounds of formula (XXXII) are as follows:

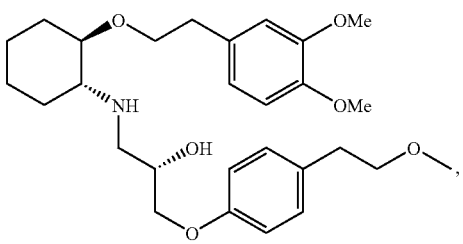

i.e., (S)-1-((1R,2R)-2-(3,4-dimethoxyphenethoxy)cyclo-
hexylamino)-3-(4-(2-methoxyethyl)phenoxy)propan-2-
ol; as well as the following isomers:
(R)-1-((1R,2R)-2-(3,4-dimethoxyphenethoxy)cyclohexy-
lamino)-3-(4-(2-methoxyethyl)phenoxy)propan-2-ol;
(S)-1-((1S,2S)-2-(3,4-dimethoxyphenethoxy)cyclohexy-
lamino)-3-(4-(2-methoxyethyl)phenoxy)propan-2-ol;
(R)-1-((1S,2S)-2-(3,4-dimethoxyphenethoxy)cyclohexy-
lamino)-3-(4-(2-methoxyethyl)phenoxy)propan-2-ol;
(S)-1-((1S,2R)-2-(3,4-dimethoxyphenethoxy)cyclohexy-
lamino)-3-(4-(2-methoxyethyl)phenoxy)propan-2-ol;
(R)-1-((1S,2R)-2-(3,4-dimethoxyphenethoxy)cyclohexy-
lamino)-3-(4-(2-methoxyethyl)phenoxy)propan-2-ol;
(S)-1-((1R,2S)-2-(3,4-dimethoxyphenethoxy)cyclohexy-
lamino)-3-(4-(2-methoxyethyl)phenoxy)propan-2-ol;
(R)-1-((1R,2S)-2-(3,4-dimethoxyphenethoxy)cyclohexy-
lamino)-3-(4-(2-methoxyethyl)phenoxy)propan-2-ol.

Examples of compounds of formula (XXXII) are as follows:

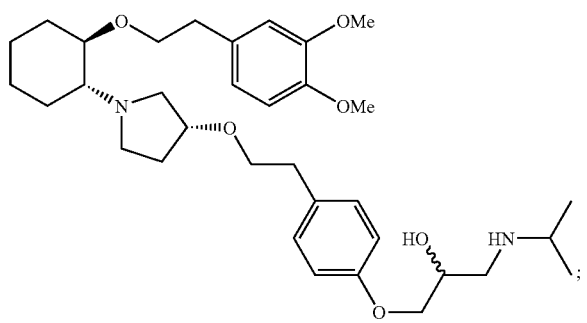

i.e., 1-(4-(2-((R)-1-((1R,2R)-2-(3,4-dimethoxyphenethoxy)
cyclohexyl)pyrrolidin-3-yloxy)ethyl)phenoxy)-3-(isopro-
pylamino)propan-2-ol; as well as the following isomers:
1-(4-(2-((S)-1-((1R,2R)-2-(3,4-dimethoxyphenethoxy)cy-
clohexyl)pyrrolidin-3-yloxy)ethyl)phenoxy)-3-(isopropy-
lamino)propan-2-ol;
1-(4-(2-((R)-1-((1S,2S)-2-(3,4-dimethoxyphenethoxy)cy-
clohexyl)pyrrolidin-3-yloxy)ethyl)phenoxy)-3-(isopropy-
lamino)propan-2-ol;
1-(4-(2-((S)-1-((1S,2S)-2-(3,4-dimethoxyphenethoxy)cy-
clohexyl)pyrrolidin-3-yloxy)ethyl)phenoxy)-3-(isopropy-
lamino)propan-2-ol;
1-(4-(2-((R)-1-((1S,2R-2-(3,4-dimethoxyphenethoxy)cyclo-
hexyl)pyrrolidin-3-yloxy)ethyl)phenoxy)-3-(isopropy-
lamino)propan-2-ol;
1-(4-(2-((S)-1-((1S,2R)-2-(3,4-dimethoxyphenethoxy)cy-
clohexyl)pyrrolidin-3-yloxy)ethyl)phenoxy)-3-(isopropy-
lamino)propan-2-ol;
1-(4-(2-((R)-1-((1R,2S)-2-(3,4-dimethoxyphenethoxy)cy-
clohexyl)pyrrolidin-3-yloxy)ethyl)phenoxy)-3-(isopropy-
lamino)propan-2-ol;
1-(4-(2-((S)-1-((1R,2S)-2-(3,4-dimethoxyphenethoxy)cy-
clohexyl)pyrrolidin-3-yloxy)ethyl)phenoxy)-3-(isopropy-
lamino)propan-2-ol.

FIG. 3 below illustrates a merged compound formed from carvedilol:

FIG. 3. Merged Compound of the Invention from Carvedilol and Compound (XXVII)

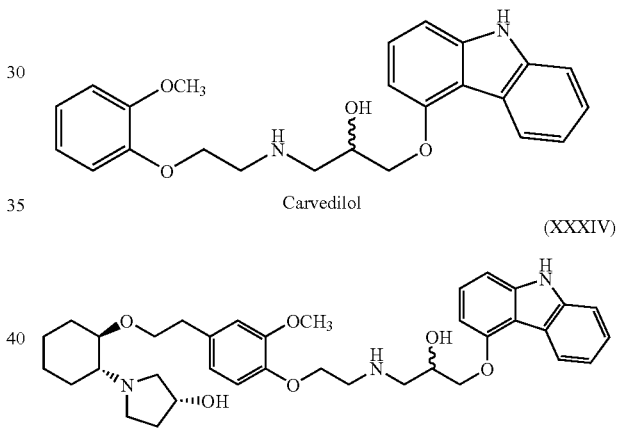

Compound (XXXIV), i.e., (R)-1-((1R,2R)-2-(4-(2-(3-
(9H-carbazol-4-yloxy)-2-hydroxypropylamino)ethoxy)-3-
methoxyphenethoxy)cyclohexyl)pyrrolidin-3-ol; are pre-
pared by this merger as well as the following isomers:
(S)-1-((1R,2R)-2-(4-(2-(3-(9H-carbazol-4-yloxy)-2-hy-
droxypropylamino)ethoxy)-3-methoxyphenethoxy)cyclo-
hexyl)pyrrolidin-3-ol;
(R)-1-((1S,2S)-2-(4-(2-(3-(9H-carbazol-4-yloxy)-2-hydrox-
ypropylamino)ethoxy)-3-methoxyphenethoxy)cyclo-
hexyl)pyrrolidin-3-ol;
(S)-1-((1S,2S)-2-(4-(2-(3-(9H-carbazol-4-yloxy)-2-hydrox-
ypropylamino)ethoxy)-3-methoxyphenethoxy)cyclo-
hexyl)pyrrolidin-3-ol;
(R)-1-((1S,2R)-2-(4-(2-(3-(9H-carbazol-4-yloxy)-2-hy-
droxypropylamino)ethoxy)-3-methoxyphenethoxy)cyclo-
hexyl)pyrrolidin-3-ol;
(S)-1-((1S,2R)-2-(4-(2-(3-(9H-carbazol-4-yloxy)-2-hydrox-
ypropylamino)ethoxy)-3-methoxyphenethoxy)cyclo-
hexyl)pyrrolidin-3-ol;
(R)-1-((1R,2S)-2-(4-(2-(3-(9H-carbazol-4-yloxy)-2-hy-
droxypropylamino)ethoxy)-3-methoxyphenethoxy)cyclo-
hexyl)pyrrolidin-3-ol;

(S)-1-((1R,2S)-2-(4-(2-(3-(9H-carbazol-4-yloxy)-2-hydroxypropylamino)ethoxy)-3-methoxyphenethoxy)cyclohexyl)pyrrolidin-3-ol.

FIG. 4 illustrates the formation of merged compounds of the invention from Atenolol:

FIG. 4. Structure of Atenolol, Compound (XXXV) and (XXXIV)

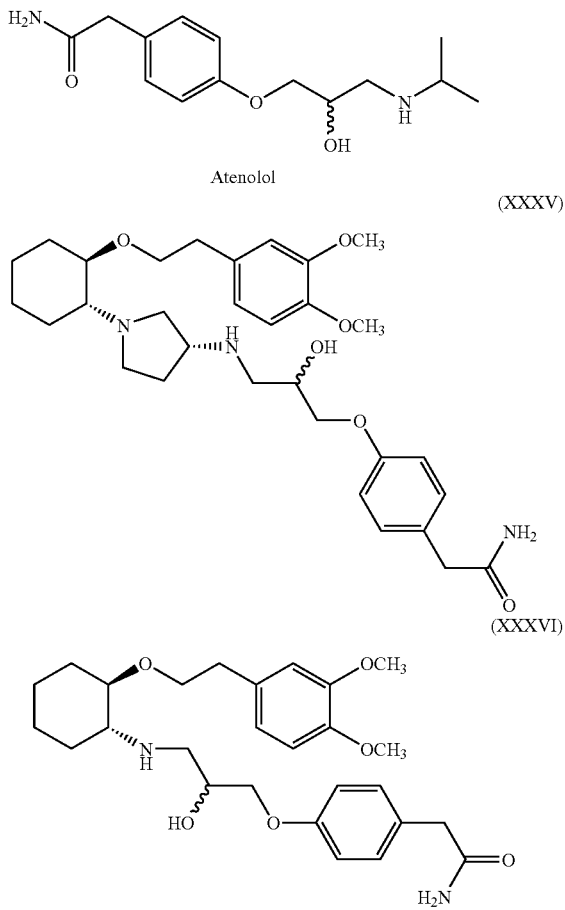

Compound (XXXV), i.e., 2-(4-(3-((R)-1-((1R,2R)-2-(3,4-dimethoxyphenethoxy)cyclohexyl)pyrrolidin-3-ylamino)-2-hydroxypropoxy)phenyl)acetamide) and Compound (XXXVI), i.e, 2-(4-(3-((1R,2R)-2-(3,4-dimethoxyphenethoxy)cyclohexylamino)-2-hydroxypropoxy)phenyl)acetamide) may be prepared from the merger of atenolol and compound (XXVII), as well as the following isomers:

2-(4-(3-((R)-1-((1S,2S)-2-(3,4-dimethoxyphenethoxy)cyclohexyl)pyrrolidin-3-ylamino)-2-hydroxypropoxy)phenyl)acetamide;

2-(4-(3-((S)-1-((1R,2R)-2-(3,4-dimethoxyphenethoxy)cyclohexyl)pyrrolidin-3-ylamino)-2-hydroxypropoxy)phenyl)acetamide;

2-(4-(3-((S)-1-((1S,2S)-2-(3,4-dimethoxyphenethoxy)cyclohexyl)pyrrolidin-3-ylamino)-2-hydroxypropoxy)phenyl)acetamide;

2-(4-(3-((R)-1-((1S,2R)-2-(3,4-dimethoxyphenethoxy)cyclohexyl)pyrrolidin-3-ylamino)-2-hydroxypropoxy)phenyl)acetamide;

2-(4-(3-((S)-1-((1S,2R)-2-(3,4-dimethoxyphenethoxy)cyclohexyl)pyrrolidin-3-ylamino)-2-hydroxypropoxy)phenyl)acetamide;

2-(4-(3-((R)-1-((1R,2S)-2-(3,4-dimethoxyphenethoxy)cyclohexyl)pyrrolidin-3-ylamino)-2-hydroxypropoxy)phenyl)acetamide;

2-(4-(3-((S)-1-((1R,2S)-2-(3,4-dimethoxyphenethoxy)cyclohexyl)pyrrolidin-3-ylamino)-2-hydroxypropoxy)phenyl)acetamide;

2-(4-((R)-3-((1R,2R)-2-(3,4-dimethoxyphenethoxy)cyclohexylamino)-2-hydroxypropoxy)phenyl)acetamide;

2-(4-((S)-3-((1R,2R)-2-(3,4-dimethoxyphenethoxy)cyclohexylamino)-2-hydroxypropoxy)phenyl)acetamide;

2-(4-((R)-3-((1S,2S)-2-(3,4-dimethoxyphenethoxy)cyclohexylamino)-2-hydroxypropoxy)phenyl)acetamide;

2-(4-((S)-3-((1S,2S)-2-(3,4-dimethoxyphenethoxy)cyclohexylamino)-2-hydroxypropoxy)phenyl)acetamide;

2-(4-((R)-3-((1S,2R)-2-(3,4-dimethoxyphenethoxy)cyclohexylamino)-2-hydroxypropoxy)phenyl)acetamide;

2-(4-((S)-3-((1S,2R)-2-(3,4-dimethoxyphenethoxy)cyclohexylamino)-2-hydroxypropoxy)phenyl)acetamide;

2-(4-((R)-3-((1R,2S)-2-(3,4-dimethoxyphenethoxy)cyclohexylamino)-2-hydroxypropoxy)phenyl)acetamide;

2-(4-((S)-3-((1R,2S)-2-(3,4-dimethoxyphenethoxy)cyclohexylamino)-2-hydroxypropoxy)phenyl)acetamide;

The synthetic procedures for the preparation of the merged ion channel modulating compounds will depend on the additional therapeutic agent that is to be incorporated into the core skeletal structure and the ion channel modulating core skeletal structure which is to be modified. The merged ion channel modulating compounds may be prepared by derivatization of an ion channel modulating compound, or by a modified synthesis of an ion channel modulating compound such that a merged ion channel modulating compound is prepared. Illustrative examples of synthetic protocols that could be used in the synthesis of the merged ion channel modulating Compounds (XXX)-(XXXIII) in FIGS. 1 and 2 above are depicted below in Schemes 1-6.

F. Administration Of The Merged Compounds Of The Invention

The present invention provides a composition or medicament that includes one or more merged compounds of the invention, selected from any of the compounds, or a solvate, pharmaceutically acceptable salt, ester, amide, complex, chelate, stereoisomer, stereoisomeric mixture, geometric isomer, crystalline or amorphous form, metabolite, metabolic precursor or merged compound thereof, as isolated enantiomeric, diastereomeric and geometric isomers thereof, and mixtures thereof, described above, in combination with a pharmaceutically acceptable carrier, diluent or excipient, and further provides a method for the manufacture of such a composition or medicament.

The present invention further provides a composition or medicament that includes one or more merged compounds of the invention, selected from any of the merged compounds, or a solvate, pharmaceutically acceptable salt, ester, amide, complex, chelate, stereoisomer, stereoisomeric mixture, geometric isomer, crystalline or amorphous form, metabolite, metabolic precursor or merged compound thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, and further provides a method for the manufacture of such a composition or medicament.

In other embodiments, the present invention provides a composition or medicament that includes a compound which is (1R,2R)-2-[(3R)-hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP; and further provides a method for the manufacture of such a composition or medicament.

The present invention further provides a composition or medicament that includes one or more merged compounds of the invention, selected from any of the merged compounds, or a solvate, pharmaceutically acceptable salt, ester, amide, complex, chelate, stereoisomer, stereoisomeric mixture, geometric isomer, crystalline or amorphous form, metabolite, metabolic precursor or merged compound thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 0.1 mg/mL to 100 mg/mL in sodium citrate of about 1 to 400 nM at a pH of about 7.5 to 4.0; and further provides a method for the manufacture of such a composition or medicament.

The present invention further provides a composition or medicament that includes one or more merged compounds of the invention, selected from any of the merged compounds, or a solvate, pharmaceutically acceptable salt, ester, amide, complex, chelate, stereoisomer, stereoisomeric mixture, geometric isomer, crystalline or amorphous form, metabolite, or metabolic precursor, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 5 mg/mL to 80 mg/mL in sodium citrate of about 10 to 80 nM at a pH of about 6.5 to 4.5; and further provides a method for the manufacture of such a composition or medicament.

The present invention further provides a composition or medicament that includes one or more merged compounds of the invention, selected from any of the merged compounds, or a solvate, pharmaceutically acceptable salt, ester, amide, complex, chelate, stereoisomer, stereoisomeric mixture, geometric isomer, crystalline or amorphous form, metabolite, or metabolic precursor thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 10 mg/mL to 40 mg/mL in sodium citrate of about 20 to 60 nM at a pH of about 6.0 to 5.0; and further provides a method for the manufacture of such a composition or medicament.

The present invention further provides a composition or medicament that includes one or more merged compounds of the invention, selected from any of the merged compounds, or a solvate, pharmaceutically acceptable salt, ester, amide, complex, chelate, stereoisomer, stereoisomeric mixture, geometric isomer, crystalline or amorphous form, metabolite, or metabolic precursor thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 20 mg/mL in sodium citrate of about 40 nM at a pH of about 5.5; and further provides a method for the manufacture of such a composition or medicament.

In another embodiment, the present invention provides compositions which include a compound of the present invention in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a compound of the present invention, in admixture with a pharmaceutically acceptable carrier, excipient or diluent. The invention further provides a pharmaceutical composition containing an effective amount of compound of the present invention, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a compound of the present invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydroxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active aminocyclohexyl ether compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocyclohexyl ether compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the aminocyclohexyl ether compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of merged compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment and/or prevention of arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Aizheimer's disease, dementia and other mental disorders, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer or other diseases. Other agents known to cause libido enhancement, analgesia or local anesthesia may be combined with compounds of the present invention.

The compositions may be prepared by methodology well known in the pharmaceutical art. The aminocyclohexyl ether compounds of the present invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the aminocyclohexyl ether compound of the present invention with water, and preferably buffering agents, so as to form a solution. The water is preferably sterile pyrogen-free water. A surfactant may be added to facilitate the formation of a homogeneous solution or suspension. Surfactants are compounds that non-covalently interact with the aminocyclohexyl ether compound so as to facilitate dissolution or homogeneous suspension of the aminocyclohexyl ether compound in the aqueous delivery system. Surfactants are desirably present in aqueous compositions of the invention because the aminocyclohexyl ether compounds according to the present invention may be hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

G. Utility and Testing of The Merged Compounds of The Invention

The present invention provides one or more merged compounds of ion channel modulating compounds, or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above, for use in methods for modulating ion channel activity in a warm-blooded animal or for modulating ion channel activity in vitro. In one version of this embodiment, the warm-blooded animal in which the ion channel activity is modulated is a mammal; in one version, the warm-blooded animal is a human; in one version, the warm-blooded animal is a farm animal.

As disclosed within the present invention, a variety of cardiac pathological conditions may be treated and/or prevented by the use of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above. These compounds of the present invention are ion channel modulating compounds that either singly or together with one or more additional compounds are able to selectively modulate certain ionic currents. The ion currents referred to herein are generally cardiac currents and more specifically, are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The pathological conditions that may be treated and/or prevented by the present invention may include, but are not limited to, various cardiovascular diseases.

The cardiac, pathological conditions that may be treated and/or prevented by the present invention may include, but are not limited to, arrhythmias such as the various types of atrial and ventricular arrhythmias, e.g., atrial fibrillation, atrial flutter, ventricular fibrillation and ventricular flutter.

In one embodiment, the present invention provides merged compounds of ion channel modulating compounds that can be used to selectively inhibit cardiac early repolarising currents and cardiac sodium currents.

In another embodiment, the present invention provides merged compounds of ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity resulting from ischaemia or inflammation. Changes such as these are observed during conditions of myocardial ischaemia or inflammation and those conditions that precede the onset of arrhythmias such as atrial fibrillation.

In other embodiments, the present invention provides a method for modulating ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating ion channel activity in an in vitro setting comprising administering in vitro an effective amount of one or more merged compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said merged compound or mixture comprising compounds as described above.

In other embodiments, the present invention provides a method for blocking/inhibiting the activity/conductance of ion channel in a warm-blooded animal comprising administering to a warm-blooded animal in need thereof, an effective amount of one or more merged compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors, as isolated enantiomeric, diastereomeric and geometric isomers thereof, and mixtures thereof; or a composition or medicament that includes said merged compound or mixture comprising compounds as described above.

In other embodiments, the present invention provides a method for blocking/inhibiting the activity/conductance of ion channel in an in vitro setting comprising administering in vitro an effective amount of one or more merged compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating voltage-gated potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for modulating cardiac sodium currents activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for modulating cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the cardiac early repolarising currents referred to in the present invention comprise ionic currents which activate rapidly after depolarisation of membrane voltage and which effect repolarisation of the cell.

In other embodiments, the cardiac early repolarising currents referred to in the present invention comprise the cardiac transient outward potassium current (Ito) and/or the ultrarapid delayed rectifier current ($I_{Kur}$).

In other embodiments, the cardiac transient outward potassium current ($I_{to}$) and/or the ultrarapid delayed rectifier current ($I_{Kur}$) referred to in the present invention comprise at least one of the Kv4.2, Kv4.3, Kv2.1, Kv1.4 and Kv1.5 currents.

In other embodiments, the present invention provides a method for treating and/or preventing arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

As noted above, the present invention provides for utilizing the compounds described above in in vitro and in vivo methods. In one embodiment, ion channels, such as cardiac potassium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating and/or preventing a variety of diseases or disorders caused by defective or inadequate function of the ion channels. The merged compounds of the invention are found to have significant activity in modulating various ion channel activity both in vivo and in vitro.

In one embodiment, the present invention provides a compound of the present invention or a composition containing said compound, for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems.

In one embodiment, the invention provides a compound of the present invention, or composition containing said compound, for use in methods for either modulating activity of ion channel(s) in a warm-blooded animal or for modulating activity of ion channel(s) in vitro, wherein said ion channel(s) correspond to some of the cardiac and/or neuronal ion channels that are responsible for one or more early repolarising currents comprising those which activate rapidly after membrane depolarisation and which effect repolarisation of the cells.

In another embodiment, of the present invention, the above-mentioned early repolarising currents comprise the transient outward potassium current ($I_{to}$ for cardiac or $I_A$ for neuronal) and/or the ultrarapid delayed rectifier current ($I_{Kur}$); and include at least one of the Kv4.2, Kv4.3, Kv2.1, Kv1.3, Kv1.4 and Kv1.5 currents.

In another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to either the cardiac or neuronal ion channel(s) that are responsible for Kv1.5 current.

In yet another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to the potassium channel that are responsible for Kv4.2 current.

Furthermore, the voltage-activated sodium ion channels comprise the $Na_v1$, $Na_v2$ or $Na_v3$ series and may be present in cardiac, neuronal, skeletal muscle, central nervous and/or peripheral nervous systems (e.g., hH1Na).

For cardiac sodium channels, in studies on ion channels in isolated human atrial myocytes, compounds of the present invention have been shown to produce frequency-dependent blockade of cardiac sodium channels. In these studies enchanced blockade of cardiac sodium channels was observed at faster rates of stimulation with sodium block increasing several-fold during rapid stimulation rates. These protocols have been designed to mimic the short recovery intervals during fibrillation.

As noted earlier, modulating the activity of an ion channel as used above may imply but does not limit to blocking or inhibiting the conductance of the current through the ion channel.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of the present invention, or a composition containing a compound of the present invention is administered to a warm-blooded animal in need thereof. Some of the diseases and conditions to which the compounds, compositions and methods of the present invention may be applied are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Alzheimer's disease, dementia and other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

Furthermore, the present invention provides a method for producing analgesia or local anesthesia in a warm-blooded animal which includes administering to a warm-blooded animal in need thereof an effective amount of a compound of the present invention or a pharmaceutical composition containing said compound. These methods may be used to relieve or forestall the sensation of pain in a warm-blooded animal.

The invention further provides a method for enhancing libido in a warm-blooded animal which includes administering to a warm-blooded animal in need thereof an effective amount of a compound of the present invention or a pharmaceutical composition containing said compound. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

Furthermore, the present invention provides a method in an in vitro setting, wherein a preparation that contains ion channels is contacted with an effective amount of an aminocyclohexyl ether compound of the invention. Suitable preparations containing cardiac sodium channels and/or cardiac potassium channels include cells isolated from cardiac tissue as well as cultured cell lines. The step of contacting includes, for example, incubation of ion channels with a compound under conditions and for a time sufficient to permit modulation of the activity of the channels by the compound.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

In order to assess whether a compound has a desired pharmacological activity with the present invention, it may be subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P—R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests may be performed using rat tissue. In order to ensure that a compound is not having effects which are only specific to rat tissue, further experiments may be performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle as applied to the shaved back of a guinea pig (*Cavia porcellus*) is assessed following subcutaneous administration of sufficient (50 μL, 10 mg/mL) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing may be carried out at intervals for up to 8 hours or more post-administration. The sites of bleb formation are examined after 24 hours to check for skin abnormalities consequent to local administration of test substances or of the vehicle used for preparation of the test solutions.

H. Preparation of The Merged Compounds of The Invention

It is understood that in the following description, combinations of substituents and/or variables of any depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of merged compounds of this invention may not possess pharmacological activity as such, they may be administered to a mammal and thereafter metabolized in the body to form compounds of the invention which are pharmacologically active. Such derivatives may therefore be described as "merged compounds". All merged compounds of compounds of this invention are included within the scope of the invention.

The following reaction schemes and examples illustrate methods to make merged compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. If applicable, the following parameters were determined:

The reaction steps as described below may be used in the preparation of the conjugates, or alternate reaction steps may be used. Alternate reaction steps would be readily recognized by one of skill in the art and include the reaction steps described "Comprehensive Organic Transformations: A Guide to Functional Group Preparations", Richard C. Larock, Wiley-VCH: 1999 and in "March's Advanced Organic Chemistry: Reactions, Mechanisms and Structure", Jerry March & Michael Smith, John Wiley & Sons Inc: 2001.

The ion channel modulating compounds used in this invention may be prepared as described in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693; or may be prepared by methods described herein or by methods known to one skilled in the art.

Melting points were determined on a Fisher-Johns apparatus and are uncorrected. NMR spectra were acquired in the indicated solvent on a Brucker AC-200, Varian XL-300, Brucker AV-300 or AV-400. Mass spectra were recorded for EI on a Kratos MS50, for FAB/LSIMS on a Kratos Concept IIHQ and for ES on a Micromass (Waters) Quattro (I) MSMS, connected to a HP1090 Series 2 LC (Agilent), controlled by Masslynx version 3.3 software. Elemental analyses were performed on an Element Analyzer 1108 by D. & H. Malhow, University of Alberta, Edmonton, A B (where analyses were indicated only by symbols of the elements, analytical results were within ±0.4% of the theoretical values). Whenever elemental analyses were not available, purity was determined by HPLC and capillary electrophoresis (CE). HPLC analyses were performed using a Gilson HPLC system (Gilson, Middleton, Wis.) with UV detection at 200 nm. A $C_{18}$ column with 150×4.6 mm, 5µ particle size was used. The mobile phase was delivered isocratically or as a gradient at a flow rate of 1 mL/min and consisted of a combination of phosphate buffer (low or high pH) and acetonitrile. Samples were prepared at ~100 µg/mL in mobile phase and 20 µL were injected into the HPLC. Purity was expressed in area %. CE analyses were performed using a P/ACE System MDQ (Beckman Coulter, Fullerton, Calif.). Uncoated silica capillaries with 60 (50 to detector) cm length and 75 µm internal diameter were used. The run buffer used was 100 mM sodium phosphate (pH 2.5). The separation voltage was either 23 or 25 kV (normal polarity) and the capillary cartridge temperature was maintained at 20° C. Samples (~0.5 mg/mL in water) were injected by pressure at 0.5 psi for 6 seconds. Detection was by UV at 200 or 213 nm. Purity was expressed in area %. IR spectral data were recorded on a Perkin-Elmer 983G spectrophotometer. Optical rotations were performed by F. Hoffman-La Roche Ltd (CH, Basel). Thin layer chromatography (TLC) was performed on E. Merck, TLC aluminum sheets 20×20 cm, Silica gel 60 $F_{254}$ plates. Flash chromatography was performed on E. M. Science silica gel 60 (70-230 mesh). Dry flash chromatography was performed with Sigma silica gel type H. Chromatotron chromatography (Harisson Research, USA) was performed on 4 mm plate with EM Science silica gel 60P $F_{254}$ with Gypsum or aluminum oxide 60P $F_{254}$ with Gypsum (type E). Preparative HPLC were performed on a Waters Delta Prep 4000 with a cartridge column (porasil, 10 µm, 125 Å, 40 mm×100 mm). GC analyses were performed on a Hewlett Packard HP 6890 equipped with 30 m×0.25 mm×0.25 µm capillary column HP-35 (crosslinked 35% PH ME siloxane) and a flame-ionization detector. High-boiling solvents (DMF, DMSO) were Sure/Seal™ from Aldrich, and tetrahydrofuran (THF) and ethylene glycol dimethyl ether (DME) were distilled from sodium-benzophenone ketyl. Organic extracts were dried with $Na_2SO_4$ unless otherwise noted. All moisture sensitive reactions were performed in dried glassware under a nitrogen or argon atmosphere.

Although anyone skilled in the art is capable of preparing the compounds of the invention according to the general techniques disclosed above, more specific details on synthetic techniques for compositions of the invention are provided elsewhere in this specification for convenience. Again, all reagents and reaction conditions employed in synthesis are known to those skilled in the art and are available from ordinary commercial sources.

The following Preparations provide preparations for the starting materials and intermediates used in the following Synthetic Examples.

PREPARATION 1

N-TERT-BUTOXYCARBONYL-3R-BENZYLOXY-PYRROLIDINE (2R)

A suspension of sodium hydride (8.08 g, 269 mmol, 80%) in anhydrous THF (100 mL) was stirred, allowed to settle and the supernatant was discarded. The grey residue was washed with THF (2×50 mL) and then re-suspended in THF (700 mL). To the cold (0° C.), stirred suspension of sodium hydride was added dropwise a solution of 1R (41.7 g, 223 mmol) in THF (200 mL) and the resultant mixture was refluxed for 1 h. After the reaction mixture had cooled to r.t., benzyl bromide (26.5 mL, 223 mmol) and tetrabutylammonium iodide (8.20 g, 22.3 mmol) were successively added. The mixture was stirred at r.t. for 18 h and then concentrated under reduced pressure. To the residue was added brine (300 mL) and water (50 mL), and the pH of the resultant mixture was adjusted to neutrality with 1M aq HCl. This mixture was extracted with hexane (100 mL), and the hexane extract was dried ($MgSO_4$ anhydr) and concentrated under reduced pressure to give 64.3 g (>98% yield) of a yellow oil, which was shown by GC analysis to consist almost exclusively of the desired product. A small amount of the oil was subjected to flash column chromatography on silica gel eluted with hexane-ethyl acetate (3:1) to give 2R as a colourless oil, which crystallized on standing. $R_f$ 0.58 ($CHCl_3$-MeOH, 4:1, v/v), $^1$H NMR (400 MHz, $CDCl_3$) δ 7.35-7.25 (m, 5H), 4.58-4.47 (m, 2H), 4.12 (br s, 1H), 3.55-3.40 (m, 4H), 2.10-2.00 (m, 1H), 2.00-1.90 (m, 1H), 1.48 (s, 9H); $^{13}$C NMR (75 MHz, $CDCl_3$) δ 154.5, 138.0, 128.3, 127.6, 79.1, 77.7, 76.8, 70.8, 51.4, 50.7, 44.0, 43.6, 31.4, 30.4, 28.4; IR (film) 2975, 1691, 1410 $cm^{-1}$; HRMS m/z calcd for $C_{16}H_{23}NO_3$ ($M_+$) 277.16779, found 277.16790.

PREPARATION 2

3R-BENZYLOXYPYRROLIDINE (3R)

A mixture of trifluoroaceic acid (50 mL) and 2R (20 g, 72 mmol) was stirred at r.t. for 1 h and then concentrated under reduced pressure. The residue was taken up in water (250 mL) and the resultant acidic aqueous solution was extracted with $Et_2O$ (2×150 mL). To the acidic aqueous layer was carefully added in portions solid $NaHCO_3$ until saturation. The basic aqueous solution was then extracted with $CH_2Cl_2$ (2×150 mL) and the combined organic extracts were dried ($Na_2SO_4$ anhydr). Evaporation of the solvent in vacuo yielded 8.0 g of 3R (62% yield). $R_f$ 0.24 ($CHCl_3$-MeOH, 9:1, v/v), $^1$H NMR (400 MHz, $CDCl_3$) δ 7.40-7.17 (m, 5H), 4.43 (s, 2H), 4.09-4.03 (m, 1H), 3.10-2.98 (m, 2H), 2.85-2.70 (m, 2H), 2.46 (s, 1H), 1.90-1.78 (m, 2H); IR (film) 3400, 1452, 1100, 1068 $cm^{-1}$.

PREPARATION 3

(1R,2R)/(1S,2S)-1-[(3R)-BENZYLOXYPYRRO-LIDINYL]CYCLOHEXAN-2-OL (4R)

A mixture of cyclohexene oxide (12.5 mL, 120.9 mmol), 3R (14.3 g, 80.6 mmol) and water (6 mL) was heated at 80° C. for 9.5 h, after which GC analysis revealed complete consumption of 3R. The reaction mixture was allowed to cool to r.t. and diluted with water (140 mL). By the addition of 1M aq HCl (55 mL), the pH was adjusted to 4.6 and the mixture was extracted with $Et_2O$ (2×200 mL). After the aqueous layer was adjusted to pH 12.5 by the addition of 40% aq NaOH (NaCl may be added to effect separation into 2 clear layers), it was extracted with $Et_2O$ (1×400 mL, 1×200 mL). The combined $Et_2O$ extracts (from basic aqueous layer) were dried ($Na_2SO_4$ anhydr), and concentrated under reduced pressure and then in vacuo at 55° C. with stirring, to give 4R as an orange oil (15.9 g, 72%) of 96% purity (GC). $R_f$ 0.24 (EtOAc-iPrNH$_2$, 98:2, v/v); $^1$H NMR (200 MHz, $CDCl_3$) δ 7.4-7.2 (m, 5H), 4.5 (s, 2H), 4.2-4.0 (m, 1H), 3.9 (br s, 1H), 3.4-3.2 (m, 1H), 3.0-2.5 (m, 4H), 2.4 (t, J 10 Hz, 1H), 2.2-1.9 (m, 2H), 1.9-1.6 (m, 4H), 1.3-1.1 (m, 4H); $^{13}$C NMR (75 MHz, $CDCl_3$) δ 138.30, 128.35, 127.61, 127.55, 77.98, 77.71, 71.07, 71.01, 70.52, 70.45, 64.96, 64.89, 54.16, 52.74, 46.83, 45.43, 33.24, 31.53, 31.34, 25.20, 24.13, 21.40, 21.33; IR (film) 3450 (broad) $cm^{-1}$.

PREPARATION 4

(1R,2R)/(1S,2S)-1-[(3R)-BENZYLOXYPYRRO-LIDINYL]-2-CHLOROCYCLOHEXANE (5R)

To a chilled (0° C.) solution of 4R (16.151 g, 58.7 mmol) and $Et_3N$ (1.25 eq., 10.2 mL, 73.4 mmol) in anhydrous $CH_2Cl_2$ (250 mL) was added dropwise neat methanesulfonyl chloride (5.65 mL, 73.4 mmol). The reaction mixture was stirred at 0° C. for 30 min and then at r.t. for 20 h. The reaction mixture was concentrated in vacuo, and the resulting residue was partitioned between a mixture of $H_2O$-2M $NaHCO_3$ aq (1:1, v/v, 150 mL) and diethyl ether (150 mL). The aqueous layer was separated and extracted twice more with diethyl ether (2×150 mL). The organic extracts were combined and dried over anhydrous magnesium sulfate. Concentration of the organic layer in vacuo and further removal of residual volatile materials under high vacuum yielded the crude chloride as a viscous oil (15.25 g). $R_f$ 0.81 (EtOAc-iPrNH$_2$, 95:5, v/v); $^1$H NMR (300 MHz, $CDCl_3$) δ 7.36-7.22 (m, 5H, Ar), 4.53-4.41 (m, 2H, AB coupling), 4.19-4.02 (m, 2H), 3.14-2.97 (m, 1H), 2.92-2.53 (m, 4H), 2.38-2.18 (m, 1H), 2.18-1.80 (m, 3H), 1.79-1.60 (m, 3H), 1.52-1.20 (m, 3H); $^{13}$C NMR (75 MHz, $CDCl_3$, APT) δ 138.36(+), 128.26 (−), 127.54 (−), 127.44 (−), 77.81/77.70(−), 70.92/70.83(+), 65.04164.91(−), 61.32/61.16(−) 56.39/56.29(+), 54.96 (+), 48.86 (+), 47.54/47.36(+), 33.36/33.18(+), 31.21 (+), 24.76124.68(+), 23.19/23.06(+), 22.48/22.40(+); MS (ES) [M+H, $Cl^{35}$]$^+$ 294.0 [M+H, $Cl^{37}$]$^+$ 296.0

PREPARATION 5

4-BENZYLOXY-3-METHOXYPHENETHYL ALCOHOL (2A)

A mixture of homovanillyl alcohol (100 mmol, 17.0 g), benzyl bromide (105 mmol, 18.33 g) and 5 M aqueous NaOH (24 mL) in ethanol (200 mL) was refluxed for 6 h. The organic solvent was evaporated in vacuo. The residue was partitioned between brine (200 mL) and diethyl ether (200 mL). The aqueous layer was separated from the organic layer and extracted again with ether. The combined organic layers were dried over MgSO$_4$ and the solvent was evaporated in vacuo. Purification by dry-column chromatography with mixtures of ethyl acetate-hexanes (1:4, 1:3, v/v) yielded 20.66 g (80% yield) of 2a as pale yellow oil. R$_f$ 0.25 (EtOAc.hexanes, 1:1, v/v); $^1$H-NMR (300 MHz, CDCl$_3$) δ 7.44-7.25 (m, 5H, Ar), 6.84-6.67 (m, 3H, Ar), 5.12 (s, 2H, PhCH$_2$O), 3.88 (s, 3H, CH$_3$O), 3.81 (t, 2H, CH$_2$CH$_2$OH), 2.79 (t, 2H, CH$_2$CH$_2$OH), 1.54 (s, 1H, OH); $^{13}$C-NMR (75 MHz, CDCl$_3$, APT) δ 149.63 (+), 146.75 (+), 137.21 (+), 131.60 (+), 128.43 (−), 127.70 (−), 127.17 (−), 120.84 (−), 114.25 (−), 112.74 (−), 71.07 (+), 63.58 (+), 55.90 (−), 38.67 (+).

PREPARATION 6

(1R,2R)/(1S,2S)-1-(4-BENZYLOXY-3-METHOXYPHENETHOXY)-2-[(3R)-BENZYLOXYPYRROLIDINYL]CYCLOHEXANE (3A)

To a suspension of NaH (2.07 g, 80% dispersion in mineral oil, 69 mmol, Acros#24710-2500) in anhydrous ethylene glycol dimethyl ether (100 mL) was added a solution of 4-benzyloxy-3-methoxyphenethyl alcohol (17.05 g, 66 mmol, 2a) in ethylene glycol dimethyl ether (100 mL). The resultant mixture was then stirred at r.t. for 30 min. to complete formation of the sodium alkoxide. The chloride (5R, 19.4 g, 66 mmol) in anhydrous ethylene glycol dimethyl ether (50 mL) was added quickly to the mixture containing the alkoxide and the resultant mixture was refluxed under Ar(g) for 16 h. The reaction mixture was allowed to cool to r.t. and then quenched with water (250 mL), followed by concentration under reduced pressure. The resultant aqueous solution was adjusted to pH0.6 by the addition of 37% aqueous HCl (22 mL) diluted with H$_2$O (28 mL). To remove unreacted 4-benzyloxy-3-methoxyphenethyl alcohol, the acidic aqueous layer was extracted with ether (3×300 mL, 350 mL). The aqueous solution was then adjusted to pH13 by the addition of 40% aqueous NaOH (24 mL) and extracted with ether (2×300 mL). The ether extracts at pH13 were combined and dried (Na$_2$SO$_4$ anhydr). Removal of solvent in vacuo yielded 25.7 g (83% yield) of the crude title compound as an orange oil. R$_f$ 0.44 (EtOAc-iPrNH$_2$, 98:2, v/v); $^1$H NMR (300 MHz, CDCl$_3$) δ 7.43-7.24 (m, 10H, Ar), 6.79-6.66 (m, 3H, Ar), 5.10 (s, 2H, PhCH$_2$O), 4.45 (d, 2H, PhCH$_2$O), 4.05 (m, 1H), 3.85 (s, 3H, CH$_3$O), 3.75-1.18 (m, 20H); $^{13}$C NMR (75 MHz, CDCl$_3$, APT) δ 149.45 (+), 146.53 (+), 138.56 (+), 137.41 (+), 132.72 (+), 128.46 (−), 128.32 (−), 127.70 (−), 127.63 (−), 127.46 (−), 127.24 (−), 120.80 (−), 114.20 (−), 112.99 (−), 79.26 (−), 77.88 (−), 71.18 (+), 70.95 (+), 70.89 (+), 69.74 (+), 64.00 (−), 57.57 (+), 56.94 (+), 55.96 (−), 49.88 (+), 49.26 (+), 36.52 (+), 31.29 (+), 28.73 (+), 27.02 (+), 23.16 (+), 22.82 (+).

PREPARATION 7

(1R,2R)/(1S,2S)-1-(4-HYDROXY-3-METHOXYPHENETHOXY)-2-[(3R)-HYDROXYPYRROLIDINYL]CYCLOHEXANE MONOHYDROCHLORIDE (4A)

(a) To a 100 mL Schlenk-flask charged with a solution of 3a (1.25 g, 2.42 mmol) in ethanol (12 mL) was added Pd—C catalyst (400 mg) and aqueous 6 M hydrochloric acid (0.8 mL). The reaction mixture was stirred vigorously overnight (20 h) at r.t. under a positive pressure of H$_2$(g). TLC and GC analyses indicated total consumption of substrate and clean conversion into the desired product. The reaction mixture was filtered through a syringe filter (PTFE, pore size: 0.2 µm; diameter: 25 mm. VWR# 28195-868) and rinsed with methanol.

(b) The acidic alcoholic solution was concentrated under reduced pressure to yield the title compound as a hygroscopic solid (840 mg, 93% yield). Further trituration of 0.38 g of the title compound in diethyl ether yielded 0.34 g of non-hygroscopic white solid. R$_f$ 0.10 (EtOAc-iPrNH$_2$, 98:2, v/v); $^1$H NMR (free amine, 300 MHz, CDCl$_3$) δ 6.81-6.66 (m, 3H, Ar), 4.21-4.17 (m, 1H, OH), 3.84 (s, 3H, CH$_3$), 3.75-1.18 (m, 20H); $^{13}$C NMR (free amine, 75 MHz, APT, CDCl$_3$) δ 146.28 (+), 143.95 (+), 131.24 (+), 121.49 (−), 114.17 (−), 111.67 (−), 79.42/79.18 (−), 71.27/71.03 (−), 69.80/69.65 (+), 63.28 (−), 59.79/59.28 (+), 55.89 (−), 48.63/48.33 (+), 36.55 (+), 34.43/34.27 (+), 28.93 (+), 27.36/27.14 (+), 23.43/23.35 (+), 23.04/22.98 (+); MS (ESI) [M+H]$^+$ 336.4 (100).

PREPARATION 8

(1R,2R)/(1S,2S)-1-(2-{2-[4-(2-HYDROXY-3-ISOPROPYLAMINO-PROPOXY)-3-METHOXY-PHENYL]-ETHOXY}-CYCLOHEXYL)-PYRROLIDIN-3-OL (XXX)

A solution of (1R,2R)/(1S,2S)-1-(4-hydroxy-3-methoxyphenethoxy)-2-[(3R)-hydroxypyrrolidinyl]cyclohexane (4a, 1.812 g, 5.4 mmol) in 5M NaOH (1.25 eq, 7.0 mmol, 1.5 mL) was mechanically stirred at room temperature for 1.5 h. To this solution was added epichlorohydrin (8.0 mmol, 0.74 g, 620 µL) and the mixture was stirred at r.t. overnight (20 h). An additional 5 mL of 1M NaOH was added and the resulting mixture was extracted with dichloromethane (3×25 mL). The combined organic layers were dried over MgSO$_4$ and concentrated in vacuo to give a clear yellow oil (1.01 g). The oil was dissolved in N-isopropylamine (5 mL) and refluxed overnight at 80° C. The N-isopropylamine was removed under vacuum to give a brown oil. Purification by silica column chromatography (EtOAc-iPrNH$_2$, 98:2, v/v) yielded a yellow oil (849 mg, 35% yield). Rf 0.21 (EtOAc-iPrNH$_2$, 95:5, v/v); $^1$H NMR (400 MHz, CDCl$_3$) δ 6.85 (d, 1H), 6.80-6.70 (m, 2H), 4.20-4.10 (m, 1H), 4.05-3.90 (m, 2H), 3.82 (s, 3H), 3.78-3.70 (m, 1H), 3.60-3.50 (m, 1H), 3.35-3.25 (m, 1H), 2.95-2.35 (m, 10H), 2.05-1.90 (m, 2H), 1.88-1.77 (m, 1H), 1.70-1.50 (m, 3H), 1.35-1.15 (m, 4H), 1.05 (d, 6H); $^{13}$C NMR (75 MHz, CDCl$_3$) δ 149.7, 146.5, 133.5, 121.1, 115.2, 133.1/113.0, 79.4, 73.3, 71.3-70.7, 69.5/69.4, 68.4, 63.5, 59.6/59.4, 55.9, 49.2, 48.8, 48.5, 36.5, 34.4/34.3, 29.0, 27.3, 23.4, 22.9; MS (ESI+) [M+H]/z 451.3, [M+2H]/z 226.2.

PREPARATION 9

(±)-CIS-2-HYDROXY-CYCLOHEXYL BENZOATE (10)

To an argon-flushed 250 mL 2-necked round bottom flask equipped with a magnetic stir bar, argon inlet and glass stopper was charged with (±)-cis-1,2-cyclohexanediol (1.0 g, 8.6 mmol) in anhydrous THF (43 mL). To the stirring mixture was added dimethyltin dichloride (0.020 g, 0.091 mmol), K$_2$CO$_3$ (2.38 g, 17.2 mmol) and benzoyl chloride (1.45 g, 10.3 mmol). The reaction was allowed to stir at r.t. for 48 h. The reaction was quenched by the addition of water (50 mL). The THF was then removed by rotary evaporation. The remaining aqueous solution was extracted with CH$_2$Cl$_2$ (5×50 mL). The combined organic extracts were washed with brine (50 mL), dried over anhydrous MgSO$_4$ and concentrated under vacuum to afford a clear pale-yellow oil (1.85 g, 98%). R$_f$ for 2-hydroxy-cyclohexyl benzoate 0.54 (EtOAc-hexanes, 1:2, v/v); $^1$H-NMR (300 mHz, CDCl$_3$) δ 1.40 (m, 2H), 1.62 (m, 2H), 1.69 (m, 2H), 1.80 (m, 1H), 1.99 (m, 1H), 2.85 (s, 1H), 3.94 (overlapping dt, J 2.8 & 5.8 Hz, 1H), 5.20 (overlapping dt, J 2.6 & 5.4 Hz, 1H), 7.39 (m, 2H, Ar), 7.51 (m, 1H, Ar), 8.01 (m, 2H, Ar)

PREPARATION 10

3,4-DIMETHOXYPHENETHYL 2,2,2-TRICHLOROACETIMIDATE (11)

A 500 mL 2-necked round bottom flask equipped with an argon inlet, rubber septum and magnetic stir bar was charged with NaH (80% dispersion, 5.2 g, 173.3 mmol). NaH was washed with anhydrous hexanes (15 mL) prior to the addition of 50 mL of anhydrous CH$_2$Cl$_2$ and of 3,4-dimethoxyphenethyl alcohol (20.0 g, 109.8 mmol) in anhydrous CH$_2$Cl$_2$ (30 mL). The solution was allowed to stir at r.t. for 75 min. The solution was then cooled to 0° C. prior to the dropwise addition of trichloroacetonitrile (16.5 mL, 23.8 g, 164.7 mmol) at 0° C. The solution was stirred for 15 min at 0° C. and 2 hr at room temperature. Distilled water (150 mL) was slowly added dropwise to quench the reaction. The aqueous layer was then extracted with CH$_2$Cl$_2$ (4×100 mL). The combined organic extracts were washed with brine (100 mL), dried over anhydrous MgSO$_4$ and concentrated by rotary evaporation to afford a brown syrup (26.8 g, 95%). The product was allowed to solidify overnight at −20° C. R$_f$ 0.74 (EtOAc-hexanes, 1:2, v/v).

PREPARATION 11

(±)-CIS-2-(3,4-DIMETHOXYPHENETHOXY)CYCLOHEXYL BENZOATE (12)

A 250 mL round bottom flask equipped with an argon inlet and magnetic stir bar was charged with 2-hydroxycyclohexyl benzoate (7.39 g, 33.6 mmol) in anhydrous CH$_2$Cl$_2$ (50 mL). The solution was cooled to 0° C. prior to the successive addition of trimethylsilyl trifluoromethanesulfonate (3.0 mL, 1.9.4 mmol) and 3,4-dimethoxyphenethyl 2,2,2-trichloroacetimidate (16.5 g, 50.4 mmol) dissolved in anhydrous CH$_2$Cl$_2$ (30 mL). The reaction mixture was stirred at r.t. for 3 days. The reaction was then quenched by the addition of H$_2$O (100 mL). The aqueous layer was extracted with CH$_2$Cl$_2$ (3×100 mL). The combined organic extracts were washed successively with brine (2×100 mL) and distilled water (100 mL), dried over anhydrous MgSO$_4$, and concentrated under vacuum. The crude material was purified by flash column chromatography (EtOAc-hexanes, 1:7, v/v,) to afford a yellow oil (8.69 g, 67%). R$_f$ 0.77 (EtOAc-hexanes, 1:2, v/v,); $^1$H-NMR (300 mHz, CDCl$_3$) δ 1.36 (m, 2H), 1.62 (m, 4H), 1.85-2.03 (m, 2H), 2.75 (t, 2H), 3.53 (m, 1H), 3.62 (m, 1H), 3.72 (m, 2H), 3.79 (s, 6H, OCH$_3$), 6.76 (m, 3H, Ar), 7.38 (m, 2H, Ar), 7.53 (m, 1H, Ar), 8.00 (m, 2H, Ar).

PREPARATION 12

(±)-CIS-2-(3,4-DIMETHOXYPHENETHOXY)CYCLOHEXAN-1-OL (13)

To a 500 mL round bottom flask, equipped with a magnetic stir bar and a condenser, charged with 2-(3,4-dimethoxyphenethoxy)cyclohexyl benzoate (23 g, 59.9 mmol) and 2-propanol (70 mL) was added sodium hydroxide (11.48 g, 287 mmol) in water (35 mL). The reaction mixture was stirred at 65° C. for 15 h. The reaction was quenched by the removal of 2-propanol in vacuo. The remaining basic aqueous solution was then extracted with EtOAc (5×100 mL). The combined organic extracts were washed with brine (150 mL), dried over anhydrous MgSO$_4$ and concentrated under vacuo to afford a yellow oil. The crude product was purified by flash column chromatography (EtOAc-hexanes, 1:7, v/v) to give a white crystalline solid (11.37 g, 68%). R$_f$ 0.51 (EtOAc-hexanes, 1:2, v/v,). $^1$H-NMR (300 MHz, CDCl$_3$) δ 1.23-1.26 (m, 2H), 1.44-1.56 (m, 4H), 1.69-1.76 (m, 2H), 1.94 (s, 1H), 2.81 (t, 2H), 3.36 (m, 1H), 3.58 (m, 1H), 3.72 (m, 2H), 3.83 (s, 3H, OCH$_3$), 3.85 (s, 3H, OCH$_3$), 6.75 (m, 3H, Ar); MS (ESI$^+$, CH$_3$OH) [M+H]$^+$ 280.1.

PREPARATION 13

(±)-CIS-2-(3,4-DIMETHOXYPHENETHOXY)CYCLOHEXYL 4-NITROBENZENESULFONATE (14)

A 10-mL round bottom flask under nitrogen atmosphere was charged with cis-2-(3,4-dimethoxyphenethoxy)cyclohexan-1-ol (13) (80 mg, 0.28 mmol), anhydrous dichloromethane (3 mL), and anhydrous pyridine (70 μL, 0.86 mmol). After the reaction mixture was cooled to 0° C., a solution of 4-nitro-benzenesulfonyl chloride (95 mg, 0.43 mmol) in anhydrous dichloromethane (1.5 mL) was added dropwise. The reaction was stirred at 0° C. for 30 minutes, and then at room temperature until total consumption of all starting material 13 (20 h), as revealed by TLC (1:1, v/v EtOAc:hexane). The reaction mixture was diluted with dichloromethane (10 mL) and aqueous H$_2$SO$_4$ (5%, 10 mL). After the aqueous layer was extracted with CH$_2$Cl$_2$ (2×10 mL), the organic layers were combined, washed successively with diluted aqueous H$_2$SO$_4$ (5%, 10 mL) and brine (10 mL), dried (anhydrous MgSO$_4$), and concentrated in vacuo to give a yellow oil. Purification of this crude material by elution through a silica gel plug using a mixture of ethyl acetate-hexanes (1:2, v/v) afforded 14 (95 mg, 72%). R$_f$ 0.71 (EtOAc-hexanes, 1:1, v/v); $^1$H-NMR (400 MHz, CDCl$_3$) δ 1.21-1.69 (m, 8H), 2.01-2.11 (m, 1H), 2.63 (t, 2H, J 6.9 Hz), 3.36-3.38 (m, 1H), 3.43-3.57 (m, 2H), 3.83 (s, 6H, OCH$_3$), 4.84-4.86 (m, 1H), 6.63-6.69 (m, 2H), 6.75 (d, 1H, J 8.1 Hz), 8.01-8.05 (m, 2H), 8.24-8.28 (m, 2H); $^{13}$C-NMR (100 MHz, CDCl$_3$) δ 21.19, 21.57, 27.20, 29.00, 35.90, 55.76, 55.87, 69.93, 82.65, 111.07, 112.19, 120.63, 124.06, 128.92, 131.39, 143.45, 147.45, 148.68, 150.33.

The syntheses of compounds of this invention are illustrated by, but not limited to the following Synthetic Examples.

SYNTHETIC EXAMPLE 1

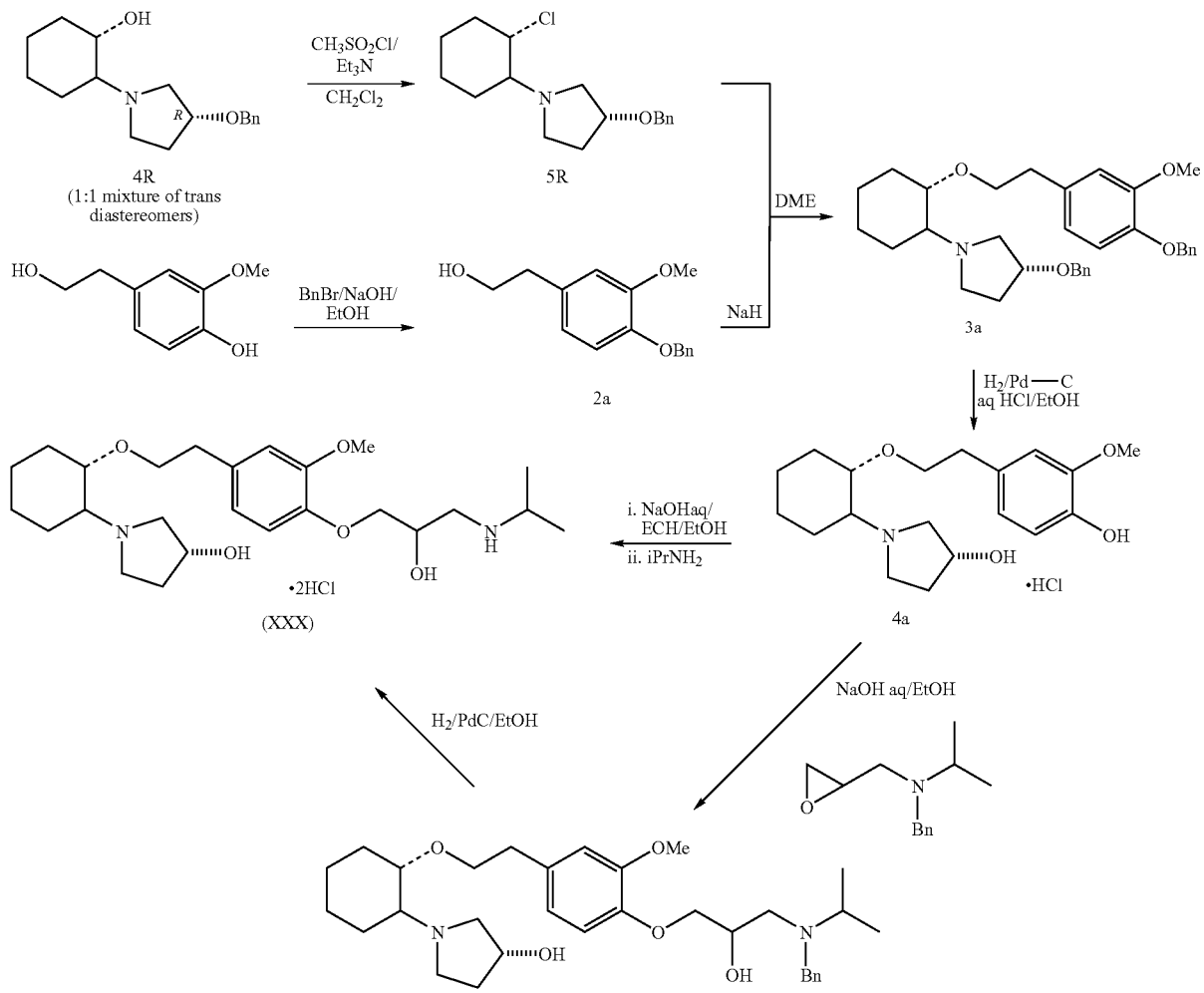

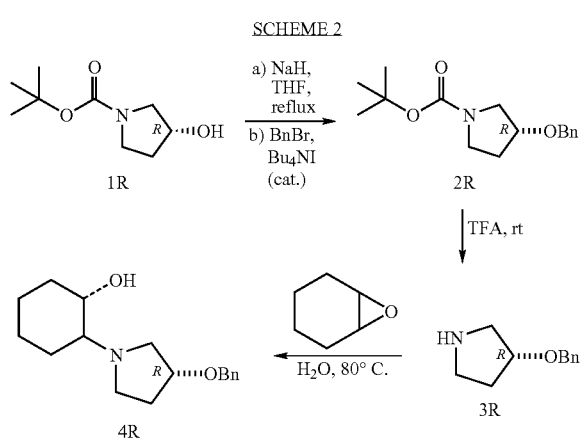

The Williamson ether synthesis (Feuer, H.; Hooz, J. Methods of Formation of the Ether Linkage. In *Patai*, Wiley: N.Y., 1967; pp 445-492) between an activated form of aminoalcohol 4R (a recent process development study (Report # DEV-CDM-001, decode Genetics, Lemont, Ill.) has established that activation of 4R with methanesulfonyl chloride resulted in the formation the chloride 5R) with the alkoxide of the appropriate phenethyl alcohol (2a) in a polar solvent such as DME (Scheme 1) provided the corresponding aminoether in high yield. Subsequent hydrogenolysis of (3a) provided 4a.

Aminoalcohols were prepared by typical $S_N2$ cyclohexene oxide opening with the secondary amine of choice in the presence of water which provides aminoalcohols with an anti relationship relative to the cyclohexane ring. More specifically, aminoalcohol 4R (Scheme 2) required the preparation of amine 3R. N-Boc-3-(R)-pyrrolidinol 1R was benzylated with benzyl bromide to give 2R, hydrolysis of the carbamate protecting group in the presence of trifluoroacetic acid provided 3R. Cyclohexene oxide ring opening with 3R in water gave aminoalcohol 4R.

Compound (XXX) is accessed in two steps from 4a as depicted in Scheme 1. Compound 4a was prepared as follows: homovanillyl alcohol was reacted with benzyl bromide in the presence of NaOH aqueous in EtOH to provide intermediate 2a. Activation of 4R via mesylation to give chloride 5R was followed by reaction with the alkoxide of 2a to provide 3a.

Debenzylation of 3a to 4a was achieved by hydrogenolysis in the presence of palladium on charcoal and concentrated HCl in a protic solvent such as EtOH. In a typical experiment, 4a reacts with NaOH in EtOH to deprotonate the phenolic functionality, then an excess epichlorohydrin is added and the mixture is stirred for 20 h. The excess epichlorohydrin is removed under vacuum and the residue is refluxed in isopropylamine to provide Compound (XXX). Alternatively, Compound (XXX) can be prepared by condensation of N-benzyl-N-isopropyl-2,3-epoxypropylamine on the same phenoxide functionality of 4a. For a method of preparation of N-benzyl-N-isopropyl-2,3-epoxypropylamine, see Hou et al. (Xue-Long Hou, Bin-Feng Li and Li-Xin Dai Synthesis of novel and enantiomerically pure epoxypropylamine: a divergent route to chiral p-adrenergic blocking agents. *Tetrahedron: Asymmetry* 1999, 10, 2319-2326).

SYNTHETIC EXAMPLE 2 lents) at a suitable temperature (e.g. about 60-70° C.) for an appropriate reaction time period (e.g. about 4-18 h) may provide 15. Hydrolysis of the carbamate group of 15 in ethereal HCl followed by neutralization and condensation with 16 in refluxing acetonitrile may give Compound (XXXI). However, an alternative preferred synthetic pathway as shown in Scheme 3 may be mono N-benzylation of N-boc-3-(R)-aminopyrrolidine via reductive amination (Panfilov, A. V.; Markovich, Yu. D.; Zhirov, A. A.; Ivashev, I. P.; Kirsanov, A. T.; Kondrat'ev, V. B. Reactions of Sodium Borohydride in Acetic Acid: Reductive Amination of Carbonyl Compounds *Pharm. Chem. J.* (*Engl. Transl.*) 2000, 34 (7), 371-373) followed by N-alkylation with allyl bromide in the presence of NaOH aqueous in EtOH. Subsequent epoxidation with m-chloroperbenzoic acid (Gregorio Asensio, Rossella Mello, Carmen Boix-Bernardini, Maria Elena Gonzlez-Nunez, and Gloria Castellano Epoxidation of primary and Secondary Alkenylammonium Salts with Dimethyloxirane, Methyl(trifluoromethyl)dioxirane, and m-Chloroperbenzoic Acid. A General

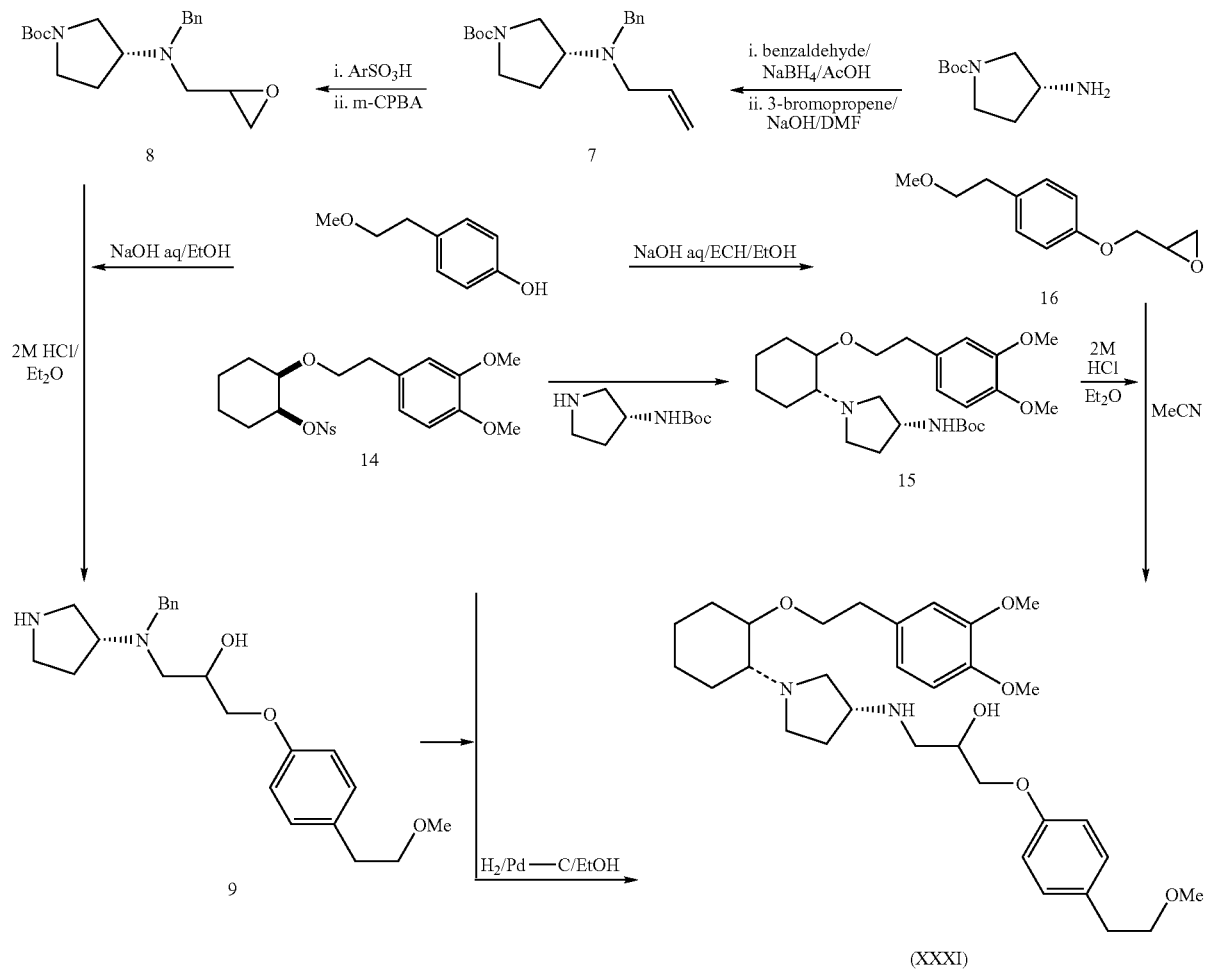

A preparation of Compound (XXXI) is depicted in Scheme 3. In one approach, 4-(2-methoxyethyl)phenol may react with epichlorohydrin (ECH) to form epoxide 16 using the same conditions as described for Compound (XXX). Nucleophilic displacement of the leaving group of 14 with an excess 3-(R)-(t-butyloxycarbonyl)aminopyrrolidine (about 3-7 equiva- Synthetic Route to Epoxyalkylamines. *J. Org. Chem.* 1995, 60, 3692-3699) or as reported by Hou et al. (for example: Esmolol, Acebutolol, Practolol, Atenolol, Celiprolol, Betaxolol, Cetamolol, Bisoprolol and Bevantolol may provide epoxide 8. The epoxide 8 may be reacted as previously described with 4-(2-methoxyethyl)phenol in the presence of NaOH aqueous in EtOH. Hydrolysis of the carbamate group in ethereal HCl may be followed by neutralization and the resultant free aminoalcohol 9 may displace the leaving group (e.g. nosylate, ONs) of 14 to give, after debenzylation, Compound (XXXI).

SYNTHETIC EXAMPLE 3

Compounds. *J. Org. Chem.* 2000, 65, 996-1002). Formation of the trichloroacetamidate 11 was accomplished by treatment of 3-4-dimethoxyphenethyl alcohol with sodium hydride and trichloroacetonitrile in dichloromethane. Ether coupling between trichloroacetamidate 11 and benzoate 10 was achieved in the presence trimethylsilyl trifluoromethanesulfonate as Lewis acid to provide intermediate 12. Saponification of 12 in the presence of aqueous NaOH and iPrOH at

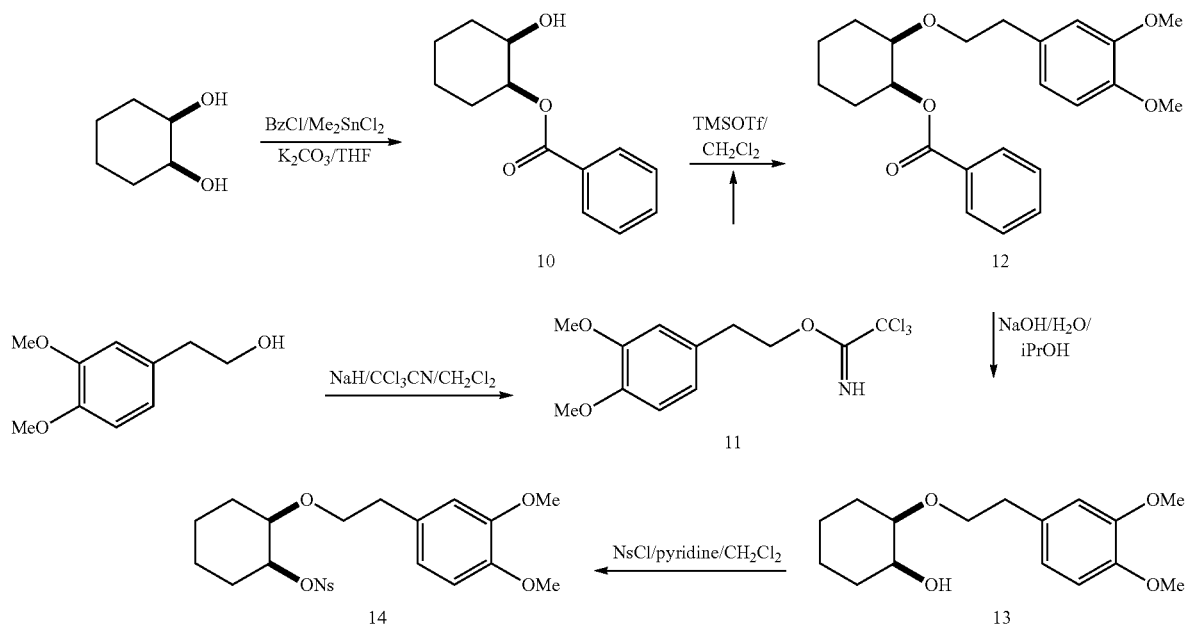

The common reactive intermediate 14 for Compounds (XXXI)-(XXXIII) was typically prepared from (±)-cis-1,2-cyclohexanediol in 5 steps (Scheme 4). Benzoylation of (±)-cis-1,2-cyclohexanediol in the presence of a catalytic amount of dimethyltin dichloride provided 10 (Fumiaki Iwasaki, Toshihide Maki, Osamu Onomura, Waka Nakashima, and Yoshihiro Matsumura Chemo- and Stereoselective Monobenzoylation of 1,2-Diols Catalyzed by Organotin about 65° C. gave hydroxyether 13. Finally, activation of the hydroxyl functionality of 13 with 4-nitro-benzenesulfonyl chloride in dichloromethane with pyridine provided the common reactive intermediate 14.

SYNTHETIC EXAMPLE 4

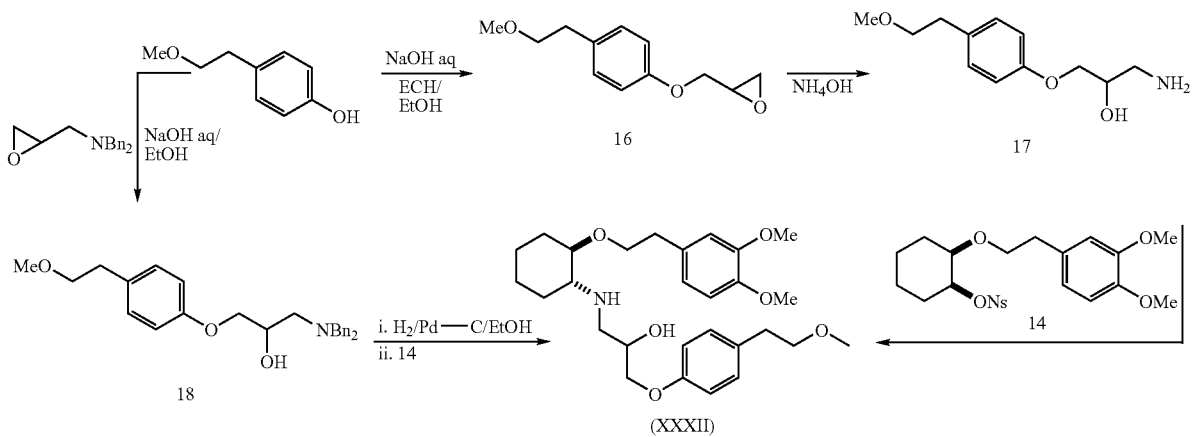

Compound (XXXII) may be prepared from 14 and 4-(2-methoxyethyl)phenol as depicted in Scheme 5. Ring epoxide opening of 16 with NH$_4$OH may give aminoalcohol 17, which then may react with 14 to yield Compound (XXXII). However, an alternative synthetic pathway may comprise preparing N,N-dibenzyl-2,3-epoxypropylamine according to Bakalarz-Jeziorna et al. (Agata Bakalarz-Jeziorna, Jan Helinski and Bozena Krawiecka Synthesis of multifunctionalized phosphonic acid esters via opening of oxiranes and azetidium salts with phosphorylsubstituted carbanions. *J. Chem. Soc., Perkin Trans.* 1, 2001, 1086-1090). Epoxide opening with 4-(2-methoxyethyl)phenol may give 18. 18 may then be N-debenzylated and followed by reaction with 14 to provide Compound (XXXII).

SYNTHETIC EXAMPLE 5 in THF. The corresponding phenethyl alcohol is reacted with sodium hydride and trichloroacetonitrile to form trichloroacetamidate 19. Ether coupling of 19 with N-boc-3-(R)-ppyrrolidinol in the presence of trimethylsilyl trifluoromethanesulfonate may provide 20. Hydrolysis of the carbamate in ethereal HCl may provide 21 after neutralization. Nucleophilic displacement of the nosylate of 14 with an excess of 21 (e.g. 3-7 equivalents) at a suitable temperature (e.g. about 60-70° C.) for an appropriate reaction time period (e.g. about 4-18 h) may provide 22. Hydrogenolysis of 22 in the presence of palladium on charcoal in EtOH followed by treatment with NaOH aqueous in EtOH and ring epoxide opening of N-benzyl-N-isopropyl-2,3-epoxypropylamine may provide Compound (XXXIII) after a last hydrogenolitic step to cleave the N-benzyl group.

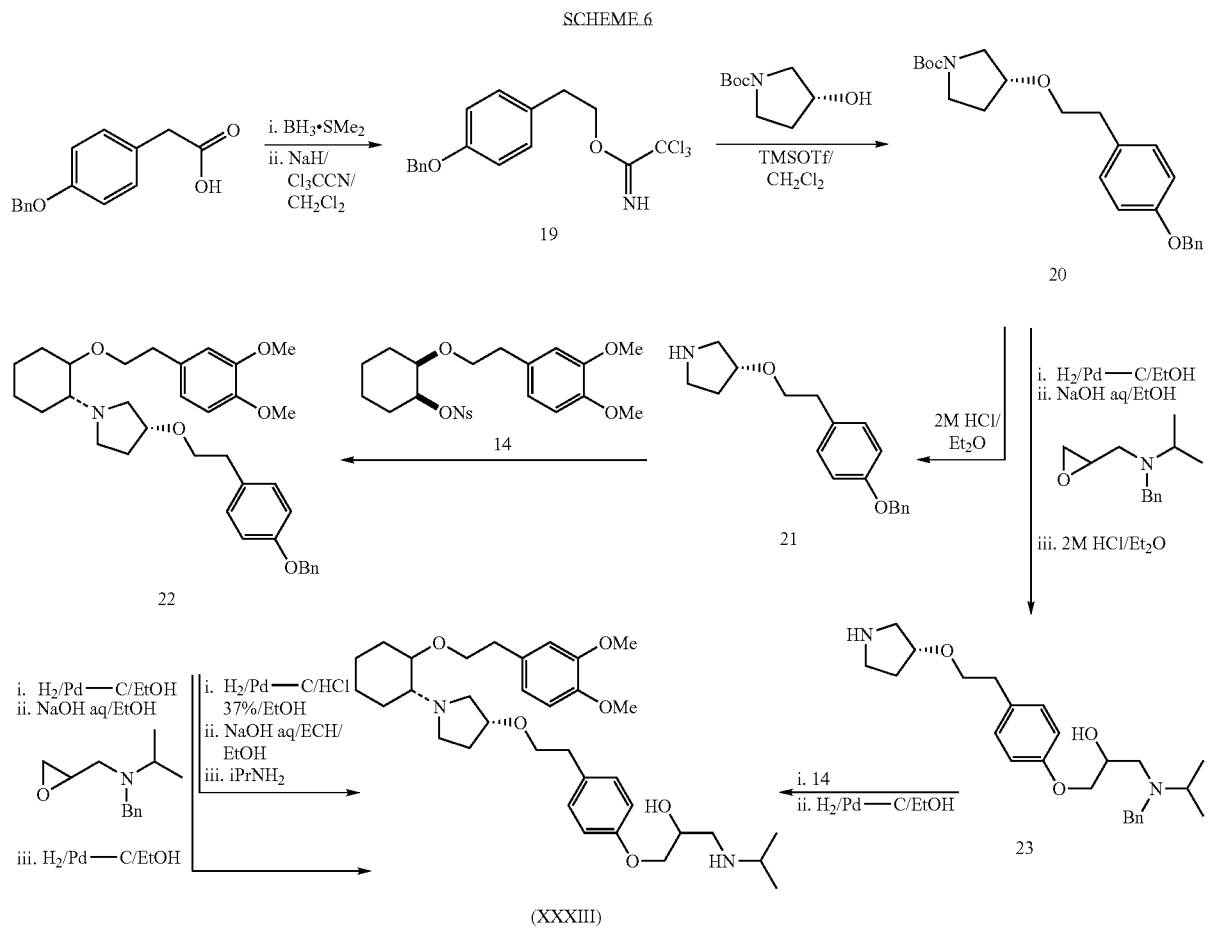

Compound (XXXIII) may be prepared from 14, N-boc-3-(R)-pyrrolidinol and 4-(benzyloxy)phenyl acetic acid as depicted in Scheme 6. There are 3 different routes depicted, the routes using N-benzyl-N-isopropyl-2,3-epoxypropylamine (for example: Esmolol, Acebutolol, Practolol, Atenolol, Celiprolol, Betaxolol, Cetamolol, Bisoprolol and Bevantolol may be preferable. Among those two routes, elaboration of the propanolamine side-chain after nucleophilic displacement of intermediate 14 with 21 may be preferred. More specifically, 4-benzyloxyphenyl acetic acid is reduced in the presence of borane-dimethyl sulfide complex

BIOLOGICAL EXAMPLE 1

Assessment of Antiarrhythmic Efficacy

Antiarrhythmic efficacy may be assessed by investigating the effect of a merged compound of the invention on the incidence of cardiac arrhythmias in anesthetized rats subjected to coronary artery occlusion. Rats weighing 200-300 gms are subjected to preparative surgery and assigned to groups in a random block design. In each case, the animal is anesthetized with pentobarbital during surgical preparation.

The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22:656 (1988).

Rats are excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

BIOLOGICAL EXAMPLE 2

Measurement of Cardiovascular and Behavioral Effects

Preparative surgery is performed in Sprague Dawley rats weighing 200-300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 guage needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 µmol/kg/min (at 1 ml/hr). This rate is doubled every 5 minutes until one of the following effects is observed:
  a) partial or complete convulsions
  b) severe arrhythmias
  c) bradycardia below 120 beats/min
  d) hypotension below 50 mmHg
  e) the dose exceeds 32 times the initial starting dose (i.e. 64 µmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lip-smacking, wet dog shake etc.) occurred are recorded.

Estimates of plasma concentrations of the test compound are determined by removing a 0.5 mL blood sample at the end of the experiment. Blood samples are centrifuged for 5 min at 4600×g and the plasma decanted. Brain tissue samples are also extracted and kept frozen (−20° C.) along with the plasma samples for chemical analysis.

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P—R interval and QRS interval indicate cardiac sodium channel blockade while the increase in Q-T interval indicates cardiac potassium channel blockade.

BIOLOGICAL EXAMPLE 3

Electrophysiological Test (In Vivo)

Male Sprague-Dawley rats weighing between 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 mL/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in µA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5× iT and 0.2 msec pulse width), MFF is the maximum stimulation frequency (in Hz) at which the heart is unable to follow stimulation (1.5× iT and (0.2 msec pulse width); VTt is the minimum pulse current (in µA) to evoke a sustained episode of VT (0.2 msec pulse width and 50 Hz) (Howard, P. G. and Walker, M. J. A, *Proc. West Pharmacol. Soc.* 33:123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R—R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 mL/hr/300 g (i.e., 0.5 μmol/kg/min). Each infusion dose is doubled (in rate) every 5 minutes. All experiments are terminated at 32 mUhr/300 g (i.e., 32 μmol/kg/min). Electrical stimulation protocols are initiated during the last two minutes of each infusion level.

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

* * * * *

All of the U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A merged compound of the formula (IXXXa):

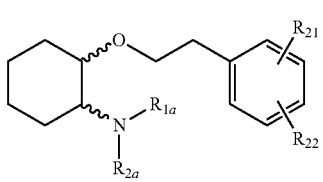

(IXXXa)

wherein:
⁓⁓⁓ indicates a bond that gives rise to either R or S stereochemistry;
$R_{1a}$ is hydrogen;
$R_{2a}$ is an aryloxypropanolamine side chain of a $β_1$-blocker or a substituted propanol-3-yl, wherein the substituted propanol-3-yl is substituted at one or more position with a group selected from hydroxyl, phenyl, or substituted phenyl wherein the substituted phenyl is substituted with $C_1$-$C_8$ alkyloxylalkyl group; and $R_{21}$ and $R_{22}$ are independently selected from a substituted or unsubstituted $C_1$-$C_8$ alkoxy group wherein the substituted $C_1$-$C_8$ alkoxy is substituted with a hydroxyl and/or a substituted or unsubstituted amino group;

as isolated enantiomeric, diastereomeric and geometric isomers thereof, and mixtures thereof.

2. The merged compound of claim 1 wherein $R_{2a}$ is a substituted substituted propanol-3-yl, wherein the substituted propanol-3-yl is substituted at one or more position with a group selected from hydroxyl, phenyl, or substituted phenyl wherein the substituted phenyl is substituted with $C_1$-$C_8$ alkyloxylalkyl group; and $R_{21}$ and $R_{22}$ are independently selected from a unsubstituted $C_1$-$C_8$ alkoxy group.

3. The merged compound of claim 2 having the following formula:

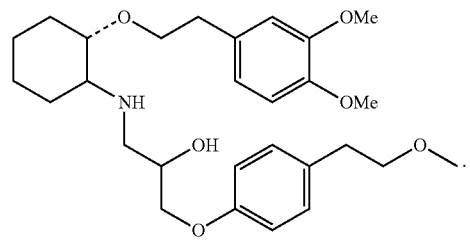

4. The merged compound of claim 2 selected from the group consisting of:
(S)-1-((1R,2R)-2-(3,4-dimethoxyphenethoxy)cyclohexylamino)-3-(4-(2-methoxyethyl)phenoxy)propan-2-ol;
(R)-1-((1R,2R)-2-(3,4-dimethoxyphenethoxy)cyclohexylamino)-3-(4-(2-methoxyethyl)phenoxy)propan-2-ol;
(S)-1-((1S,2S)-2-(3,4-dimethoxyphenethoxy)cyclohexylamino)-3-(4-(2-methoxyethyl)phenoxy)propan-2-ol;
(R)-1-((1S,2S)-2-(3,4-dimethoxyphenethoxy)cyclohexylamino)-3-(4-(2-methoxyethyl)phenoxy)propan-2-ol;
(S)-1-((1S,2R)-2-(3,4-dimethoxyphenethoxy)cyclohexylamino)-3-(4-(2-methoxyethyl)phenoxy)propan-2-ol;
(R)-1-((1S,2R)-2-(3,4-dimethoxyphenethoxy)cyclohexylamino)-3-(4-(2-methoxyethyl)phenoxy)propan-2-ol;
(S)-1-((1R,2S)-2-(3,4-dimethoxyphenethoxy)cyclohexylamino)-3-(4-(2-methoxyethyl)phenoxy)propan-2-ol; and
(R)-1-((1R,2S)-2-(3,4-dimethoxyphenethoxy)cyclohexylamino)-3-(4-(2-methoxyethyl)phenoxy)propan-2-ol.

5. A merged compound of the formula (IXXXa):

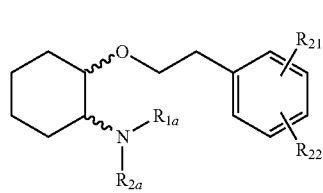

(IXXXa)

wherein:
⁓⁓⁓ indicates a bond that gives rise to either R or S stereochemistry;
$R_{1a}$ and $R_{2a}$ are taken together with the nitrogen atom to which they are attached to form a 5 to 8-membered heterocyclic ring that is optionally substituted with a group selected from a hydroxyl;
$R_{21}$ is unsubstituted $C_1$-$C_8$ alkoxy; and $R_{22}$ is a substituted $C_1$-$C_8$ alkoxy group wherein the substituted $C_1$-$C_8$ alkoxy is substituted with a hydroxyl and/or a substituted or unsubstituted amino group;

as isolated enantiomeric, diastereomeric and geometric isomers thereof, and mixtures thereof.

6. The merged compound of claim 5, wherein:

$R_{1a}$ and $R_{2a}$ are taken together with the nitrogen atom to which they are attached to form a pyrrolidino ring that is substituted with a hydroxyl group; and $R_{21}$ is a methoxy group.

7. The merged compound of claim 6 having the following formula:

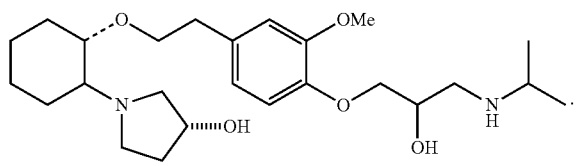

8. The merged compound of claim 7 selected from the group consisting of:

(R)-1-((1R,2R)-2-(4-(2-hydroxy-3-(isopropylamino)propoxy)-3-methoxyphenethoxy)cyclohexyl)pyrrolidin-3-ol;

(S)-1-((1R,2R)-2-(4-(2-hydroxy-3-(isopropylamino)propoxy)-3-methoxyphenethoxy)cyclohexyl)pyrrolidin-3-ol;

(R)-1-((1S,2S)-2-(4-(2-hydroxy-3-(isopropylamino)propoxy)-3-methoxyphenethoxy)cyclohexyl)pyrrolidin-3-ol;

(S)-1-((1S,2S)-2-(4-(2-hydroxy-3-(isopropylamino)propoxy)-3-methoxyphenethoxy)cyclohexyl)pyrrolidin-3-ol;

(R)-1-((1S,2R)-2-(4-(2-hydroxy-3-(isopropylamino)propoxy)-3-methoxyphenethoxy)cyclohexyl)pyrrolidin-3-ol;

(S)-1-((1S,2R)-2-(4-(2-hydroxy-3-(isopropylamino)propoxy)-3-methoxyphenethoxy)cyclohexyl)pyrrolidin-3-ol;

(R)-1-((1R,2S)-2-(4-(2-hydroxy-3-(isopropylamino)propoxy)-3-methoxyphenethoxy)cyclohexyl)pyrrolidin-3-ol; and (S)-1-((1R,2S)-2-(4-(2-hydroxy-3-(isopropylamino)propoxy)-3-methoxyphenethoxy)cyclohexyl)pyrrolidin-3-ol.

9. A merged compound of the formula (IXXXa):

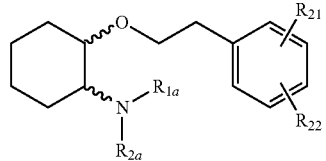

(IXXXa)

wherein:

⁓⁓ indicates a bond that gives rise to either R or S stereochemistry;

$R_{1a}$ and $R_{2a}$ are taken together with the nitrogen atom to which they are attached to form a 5 to 8-membered heterocyclic ring that is substituted with an amino or substituted amino; and $R_{21}$ and $R_{22}$ are independently selected from a substituted or unsubstituted $C_1$-$C_8$ alkoxy group wherein the substituted $C_1$-$C_8$ alkoxy is substituted with a hydroxyl and/or a substituted or unsubstituted amino group;

as isolated enantiomeric, diastereomeric and geometric isomers thereof, and mixtures thereof.

10. The merged compound of claim 9 wherein:

$R_{1a}$ and $R_{2a}$ are taken together with the nitrogen atom to which they are attached to form a 5 to 8-membered heterocyclic ring that is substituted with a substituted amino; and $R_{21}$ and $R_{22}$ are each an unsubstituted $C_1$-$C_8$ alkoxy group.

11. The merged compound of claim 10 having the following formula:

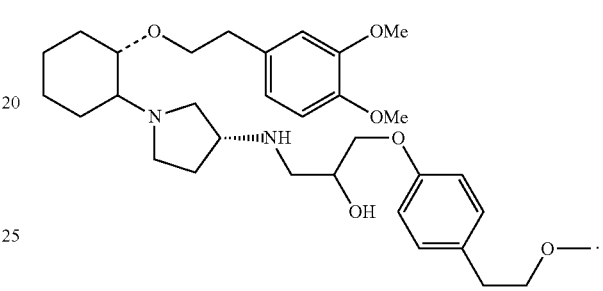

12. The merged compound of claim 11 selected from the group consisting of:

1-((R)-1-((1R,2R)-2-(3,4-dimethoxyphenethoxy)cyclohexyl)pyrrolidin-3-ylamino)-3-(4-(2-methoxyethyl)phenoxy)propan-2-ol;

1-((S)-1-((1R,2R)-2-(3,4-dimethoxyphenethoxy)cyclohexyl)pyrrolidin-3-ylamino)-3-(4-(2-methoxyethyl)phenoxy)propan-2-ol;

1-((R)-1-((1S,2S)-2-(3,4-dimethoxyphenethoxy)cyclohexyl)pyrrolidin-3-ylamino)-3-(4-(2-methoxyethyl)phenoxy)propan-2-ol;

1-((S)-1-((1S,2S)-2-(3,4-dimethoxyphenethoxy)cyclohexyl)pyrrolidin-3-ylamino)-3-(4-(2-methoxyethyl)phenoxy)propan-2-ol;

1-((R)-1-((1S,2R)-2-(3,4-dimethoxyphenethoxy)cyclohexyl)pyrrolidin-3-ylamino)-3-(4-(2-methoxyethyl)phenoxy)propan-2-ol;

1-((S)-1-((1S,2R)-2-(3,4-dimethoxyphenethoxy)cyclohexyl)pyrrolidin-3-ylamino)-3-(4-(2-methoxyethyl)phenoxy)propan-2-ol; and 1-((R)-1-((1R,2S)-2-(3,4-dimethoxyphenethoxy)cyclohexyl)pyrrolidin-3-ylamino)-3-(4-(2-methoxyethyl)phenoxy)propan-2-ol.

13. A merged compound of the formula (IXXXa):

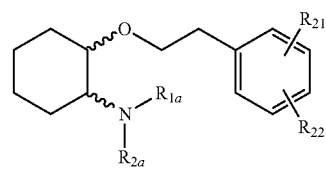

(IXXXa)

wherein:
wherein:

⁓⁓ indicates a bond that gives rise to either R or S stereochemistry;

$R_{1a}$ and $R_{2a}$ are taken together with the nitrogen atom to which they are attached to form a 5 to 8-membered heterocyclic ring that is substituted with a substituted alkoxy group wherein the substituted alkoxy group is substituted phenethoxy; and $R_{21}$ and $R_{22}$ are independently selected from a substituted or unsubstituted $C_1$-$C_8$ alkoxy group wherein the substituted $C_1$-$C_8$ alkoxy is substituted with a hydroxyl and/or a substituted or unsubstituted amino group;

as isolated enantiomeric, diastereomeric and geometric isomers thereof, and mixtures thereof.

14. The merged compound of claim 13 wherein:

$R_{1a}$ and $R_{2a}$ are taken together with the nitrogen atom to which they are attached to form a 5 to 8-membered heterocyclic ring that is substituted with a substituted alkoxy group wherein the substituted alkoxy group is substituted phenethoxy; and $R_{21}$ and $R_{22}$ are each an unsubstituted $C_1$-$C_8$ alkoxy group.

15. The merged compound of claim 14 having the following formula:

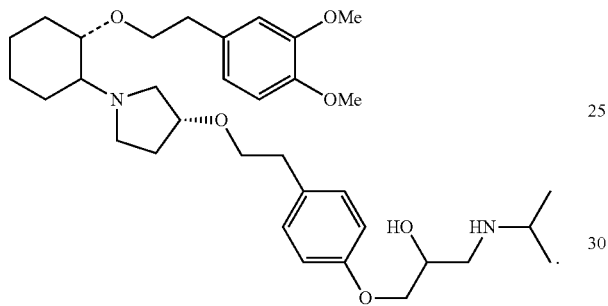

16. The merged compound of claim 15 selected from the group consisting of:

1-(4-(2-((R)-1-((1R,2R)-2-(3,4-dimethoxyphenethoxy) cyclohexyl)pyrrolidin-3-yloxy)ethyl)phenoxy)-3-(isopropylamino)propan-2-ol;

1-(4-(2-((S)-1-((1R,2R)-2-(3,4-dimethoxyphenethoxy) cyclohexyl)pyrrolidin-3-yloxy)ethyl)phenoxy)-3-(isopropylamino)propan-2-ol;

1-(4-(2-((R)-1-((1S,2S)-2-(3,4-dimethoxyphenethoxy)cyclohexyl)pyrrolidin-3-yloxy)ethyl)phenoxy)-3-(isopropylamino)propan-2-ol;

1-(4-(2-((S)-1-((1S,2S)-2-(3,4-dimethoxyphenethoxy)cyclohexyl)pyrrolidin-3-yloxy)ethyl)phenoxy)-3-(isopropylamino)propan-2-ol;

1-(4-(2-((R)-1-((1S,2R)-2-(3,4-dimethoxyphenethoxy) cyclohexyl)pyrrolidin-3-yloxy)ethyl)phenoxy)-3-(isopropylamino)propan-2-ol;

1-(4-(2-((S)-1-((1S,2R)-2-(3,4-dimethoxyphenethoxy)cyclohexyl)pyrrolidin-3-yloxy)ethyl)phenoxy)-3-(isopropylamino)propan-2-ol;

1-(4-(2-((R)-1-((1R,2S)-2-(3,4-dimethoxyphenethoxy) cyclohexyl)pyrrolidin-3-yloxy)ethyl)phenoxy)-3-(isopropylamino)propan-2-ol; and 1-(4-(2-((S)-1-((1R,2S)-2-(3,4-dimethoxyphenethoxy)cyclohexyl)pyrrolidin-3-yloxy)ethyl)phenoxy)-3-(isopropylamino)propan-2-ol.

* * * * *

UNITED STATES PATENT AND TRADEMARK OFFICE
CERTIFICATE OF CORRECTION

PATENT NO.         : 8,058,304 B2
APPLICATION NO.    : 11/547422
DATED              : November 15, 2011
INVENTOR(S)        : Lewis Siu Leung Choi et al.

It is certified that error appears in the above-identified patent and that said Letters Patent is hereby corrected as shown below:

On the Title Page

Item (75):
"Lewis S.L. Choi, Burnaby (CA); Doug Ta Hung Chou, Vancouver (CA); Grace Jung, New Westminster (CA); Bertrand M.C. Plouvier, Vancouver (CA)" should read, --Lewis S.L. Choi, Burnaby, BC (CA); Doug Ta Hung Chou, Vancouver, BC (CA); Grace Jung, New Westminster, BC (CA); Bertrand M.C. Plouvier, Vancouver, BC (CA)--.

Item (56):
"Howard and Walker, "Electrical Stimulation Studies with Quinacainol, a Putative IC Agent, in the Anaesthetised Rat", *Proc. West. Pharmacol. Soc.* 33: 123-127, 1990." should read, --Howard and Walker, "Electrical Stimulation Studies with Quinacainol, a Putative 1C Agent, in the Anaesthetised Rat", *Proc. West. Pharmacol. Soc.* 33: 123-127, 1990.--.

Signed and Sealed this
Seventh Day of August, 2012

David J. Kappos
*Director of the United States Patent and Trademark Office*